United States Patent
Ibarra et al.

(10) Patent No.: US 9,358,264 B2
(45) Date of Patent: Jun. 7, 2016

(54) EFFECTS OF A DECAFFEINATED GREEN COFFEE EXTRACT ON BODY WEIGHT CONTROL BY REGULATION OF GLUCOSE METABOLISM

(75) Inventors: Alvin Ibarra, Hoboken, NJ (US); Marc Roller, Morieres les Avignon (FR); Jacques DiKansky, Avignon (FR)

(73) Assignee: NATUREX, S.A., Avignon (FR)

(*) Notice: Subject to any disclaimer, the term of this patent is extended or adjusted under 35 U.S.C. 154(b) by 345 days.

(21) Appl. No.: 13/072,648

(22) Filed: Mar. 25, 2011

(65) Prior Publication Data

US 2011/0223281 A1 Sep. 15, 2011
US 2015/0072042 A2 Mar. 12, 2015
US 2016/0015766 A2 Jan. 21, 2016

Related U.S. Application Data

(63) Continuation-in-part of application No. 12/263,292, filed on Oct. 31, 2008, now abandoned.

(51) Int. Cl.
*A61K 36/74* (2006.01)
*A61K 31/235* (2006.01)
*A61K 45/06* (2006.01)

(52) U.S. Cl.
CPC ............ *A61K 36/74* (2013.01); *A61K 31/235* (2013.01); *A61K 45/06* (2013.01)

(58) Field of Classification Search
CPC ... A01B 12/006; A61K 45/06; A61K 31/235; A61K 36/74
See application file for complete search history.

(56) References Cited

U.S. PATENT DOCUMENTS

2005/0181044 A1* 8/2005 Romero ........................ 424/464
2007/0178176 A1* 8/2007 Kandaswami et al. ....... 424/729
2008/0096902 A1* 4/2008 Yarosh et al. ................. 514/257

OTHER PUBLICATIONS

Dellalibera et al. SVETOL, A Decaffeinated Green Coffee Extract, Induces Weight Loss and Increses the Lean Mass to Fat Mass Ratio in Overweight Volunteers; Phytotherapie (2006) No. 4, pp. 194-197.*
VitaNet, LLC: Green Coffee Extract Doctors Best SVETOL—Best Sugar Balance; (online) URL http:llvitanetonline.comlforums111Thread1890>, published online May 5, 2006, pp. 1-5.*
Clifford et al. (Hierarchical Scheme for LC-MSn Identification of Chlorogenic Acids; J. Agric. Food Chem (2003), 51, 2900-2911.*
(Continued)

*Primary Examiner* — Patricia A Leith
(74) *Attorney, Agent, or Firm* — Matthias Scholl, PC; Matthias Scholl

(57) ABSTRACT

A method of controlling body weight in humans by administering an amount of decaffeinated green coffee extract effective to treat a subject. A preferred green coffee extract contains a ratio of 4-caffeoylquinic acid (4-CQA) to total chlorogenic acids (tCGA) (5-CQA/tCGA) of from about 0.1 to about 0.2. More preferably, the green coffee extract comprises from about 6% to about 8% of 4-caffeoylquinic acid and has a total chlorogenic acid concentration that exceeds about 45%. A preferred method of administration consists of administering the green coffee extracts is a dosage of about 200 mg twice a day prior to meals on an empty stomach.

1 Claim, 15 Drawing Sheets

(56) References Cited

OTHER PUBLICATIONS

Farah et al. Effect of Roasting on the Formation of Chlorogenic Acid Lactones in Coffee; J. Agric. Food chem (2005), 53, 1505-1513.*

Vitrac et al. Contribution of Chlorogenic Acids to the Inhibition of Human Hepatic Glucose-6-Phosphatase Activity In Vitro by SVETOL, A Standardized Decaffeinated Green Coffee Extract; J. Agric. Food Chem, 2010, 58, pp. 4141-4144.*

\* cited by examiner

| CGA = Chlorogenic acid | 3-Ca = 3-cournaric acid |
| CA = Caffeic acid | 3-HPPA = 3-hydroxyphenylpropionic acid |
| QA = Quinic acid | HB = Hydroxybenzoic acid |
| Fe = Ferulic acid | HHA = Hydroxyhippuric acid |
| Isofe = Isoferulic acid | |

MUSCLE MASS/FAT MASS RATIO

WEIGHT LOSS

DECREASE OF BODY MASS INDEX

EFFECTS OF A DECAFFEINATED GREEN COFFEE EXTRACT ON BODY WEIGHT CONTROL BY REGULATION OF GLUCOSE METABOLISM

This application is a continuation-in-part and claims the benefit of a non-provisional U.S. patent application Ser. No. 12/263,292 filed on Oct. 31, 2008.

FIELD OF THE INVENTION

The present invention relates to dietary supplements comprising a green coffee extract and methods relating to the administration of green coffee extract.

BACKGROUND OF THE INVENTION

The prevalence of obesity (BMI ≥30 kg/m') continues to be a health concern for adults, children and adolescents in the United States. Data from the NHANES survey shows that among adult men the prevalence of obesity increased from 31.1% in 2003-04 to 32.2% in 2007-08, a small but not statistically significant change. Among adult women, the prevalence of obesity increased from 33.2% in 2003-04 to 35.5% in 2007-08, again a small but not significant change (Ogden et al. *Gastroenterology* 2007; 132 (6):2087-2102; Flegal et al. *JAMA* 2009; 303 (3):235-241). In Europe, the prevalence of obesity has increased by 10 to 38%, depending on the country, over the last 10 years (World Health Organization 2003; Factsheet #894). Type 2 diabetes (T2D), often associated with excess weight, affects more than 3% of the world's population, or more than 220 million people (World Health Organization 2009; Factsheet 312). This figure is projected to rise to 300 million by 2025 (Zimmet et al. *Nature* 2001; 414:782-787).

Recent epidemiological studies have shown the beneficial effect of coffee in terms of prevention of T2D, also known as fatty diabetes. T2D is a dysfunction of the mechanism that regulates blood glucose concentration, resulting in insulin resistance. This insulin resistance is expressed as abnormal and prolonged hyperglycemia. Before resulting in T2D, this hyperglycemia consists of an excess of blood glucose which can metabolize into triglycerides, hence, causing weight gain.

Caffeine consumption of 5 mg/kg/day is known to have a role in insulin resistance (Graham et al. *Can. J. Physiol. Pharmacol* 2001; 79 (7):559-565). Because coffee is the primary dietary source of caffeine, a number of epidemiological studies have been conducted to assess the correlation between the coffee consumption of different Western and Asiatic populations and the risk of occurrence of T2D.

TABLE 1

Summary of studies on the risk of type 2 diabetes as a function of coffee consumption.

| References | Origin of the population studied | Length of the study | Number of individuals monitored | Sex | Daily consumption of coffee | Decrease in risk % | P |
| --- | --- | --- | --- | --- | --- | --- | --- |
| R. M. Van Dam, 2002 | Holland | 10 years | 17,111 | Mixed | ≥7 cups | 50 | <0.0002 |
| A. Reunanen, 2003 | Finland | 4 years | 19,518 | Mixed | ≥7 cups | 8 | not reported |
| J. Tuomilehto, 2004 | Finland | 12 years | 14,629 | Mixed | ≥10 cups | 61 | <0.001 |
| E. Salazar-Martinez, 2004 | United States | 22 years | 41,934 | Men | ≥6 cups | 54 | <0.001 |
| E. Salazar-Martinez, 2004 | United States | 18 years | 84,276 | Women | ≥6 cups | 29 | <0.001 |
| R M van Dam et al, 2006 | United States | 9.8 years | 88,259 | Women | ≥4 cups | 47 | <0.0001 |
| H. Iso et al., 2006 | Japan | 5 years | 17,413 | Men & Women | ≥3 cups | 42 | <0.027 |
| M A Pereira et al., 2006 | United States | 11 years | 28,812 | Women | ≥6 cups | 21 | <0.07 |
| S. Bidel et al., 2008 | Finland | 12.5 years | 21,826 | Men & Women | ≥7 cups | 36 | <0.0001 |
| A O Odegaard et al., 2008 | Singapore | 5.7 years | 36,908 | Men & Women | ≥4 cups | 30 | <0.02 |
| M. Kato et al., 2009 | Japan | 10 years | 24,826 | Men | ≥5 cups | 18 | <0.006 |
| M. Kato et al., 2009 | Japan | 10 years | 31,000 | Women | ≥5 cups | 60 | <0.001 |
| S. van Dieren et al., 2009 | Holland | 10 years | 38,176 | Men & Women | ≥6 cups | 7 | <0.04 |
| D S Sartorelli et al., 2010 | France | 11 years | 69,532 | Women | ≥3 cups | 27 | <0.001 |

Numerous epidemiological studies, mainly published between 2002 and 2010, have demonstrated that coffee consumption of between 3 and 10 cups per day decreases the risk of developing T2D. Table 1 summarizes studies conducted in populations of greater than 10,000 people, totaling 534,220 people in six countries. The ground-breaking study was reported by van Dam et al. (*The Lancet*, 2002; 360:1477-1478) showing the influence of higher or lower coffee consumption on health. After monitoring 17,111 Dutch people between 30 and 60 years old for 7 years, they clearly established a positive correlation between coffee consumption and a decrease in the risk of T2D. Participants drinking 7 cups of coffee or more per day were half as likely (P=0.0002) than participants drinking 2 cups of coffee or less per day to develop T2D. Therefore, there is a link between high coffee consumption and a decrease in the risk of T2D.

Naismith et al. (*Nutr. Metabol.* 1970; 12:144-151) studied the effect of coffee consumption on the blood sugar concentration. Their study, carried out on twenty healthy volunteers, concluded that certain compounds, other than caffeine, significantly reduce fasting blood sugar levels. This was also suggested by Isogawa et al. (*The Lancet,* February 2003; 361:702-704). They converted the number of cups consumed into the quantity of caffeine ingested and showed that, despite the tendency to decrease the prevalence of fasting hyperglycemia, the consumption of caffeine alone had no notable effect (p=0.012). This study shows that the risk of fasting hyperglycemia is clearly lower in people consuming coffee, compared with its prevalence in tea drinkers, whatever type of preparation—green tea, fermented tea or oolong tea. No significant correlation has been established between the prevalence of fasting hyperglycemia and the consumption of tea, whether in terms of frequency of consumption or quantity of caffeine ingested. Salazar-Martinez (*Ann Intern Med.* 2004 Jan. 6; 140 (1):1-8) concluded that caffeine is not the active substance decreasing the risk of T2D. Indeed, a net decrease in the risk of T2D occurs for consumers of more than 6 cups of coffee per day. The investigators therefore concluded that molecules contained in coffee, but not caffeine alone, have a beneficial effect in terms preventing fasting hyperglycemia.

While caffeine is not the active substance that prevents blood sugar disorders, the various authors of the epidemiological studies mentioned in Table 1 suggest or agree that chlorogenic acids (CGA) do play a highly influential role in this. Current scientific consensus attributes the protective effect of chlorogenic acids to their capacity to regulate postprandial blood sugar concentration, inhibit the intestinal absorption of glucose, improve glucose tolerance, and, to a lesser extent, modulate serum lipid concentrations.

Chlorogenic acids (CGA) are a family of esters formed between certain hydroxycinnamic acids (i.e. caffeic and ferulic acids) and (−)-quinic acid. Green (or raw) coffee is a major source of CGA in nature (5-12 g/100 g) (Farah et al. *Braz J Plant Physiol.* 365 2006; 18:23-36). The major CGA in green coffee are 3-, 4- and 5-caffeoylquinic acids (3-, 4- and 5-CQA), 3,4-, 3,5- and 4,5-dicaffeoylquinic acids (3,4-, 3,5-, and 4,5-diCQA); 3-, 4- and 5-feruloylquinic acids (3-, 4- and 5-FQA) and 3-, 4- and 5-p-coumaroylqunic acids (3-, 4-, and 5-p-CoQA). Caffeoylferuloylquinic acids (CFQA) are minor CGA compounds also found in green coffee, especially in *Coffea robusta* species. Very small amounts of CGA lactones formed by heating during primary processing may also be observed (Farah et al. *Braz J Plant Physiol.* 2006; 18:23-36.- Farah et al. *J Agric Food Chem.* 2005; 53:1505-13).

Coffee berries, which contain the coffee bean, are produced by several species of small evergreen plants of the genus *Coffea*. The two most commonly grown species are *Coffea robusta* (also known as *Coffea canephora*) and *Coffea arabica*. These are cultivated in Latin America, Southeast Asia, and Africa. Concentrations on total chlorogenic acids (tCGA) are different in the two species. In general, tCGA concentration is higher in *Coffea robusta* than in *Coffea arabica*. Table 2 summarizes the content of FQA, CQA, and tCGA in the two coffee species before roasting.

TABLE 2

Content of FQA, CQA, and tCGA in the
*Coffea arabica* and *Coffea robusta*

| Phenolic acids | *Coffea arabica* g/kg | | *Coffea robusta* g/kg | |
| --- | --- | --- | --- | --- |
| | Santos | Sao Paulo | Ghana | Uganda |
| Feruloylquinic acids (FQA) | 2.3-3.3 | 0-2.1 | 11.6-12.0 | 5.4-6.8 |

TABLE 2-continued

Content of FQA, CQA, and tCGA in the
*Coffea arabica* and *Coffea robusta*

| Phenolic acids | *Coffea arabica* g/kg | | *Coffea robusta* g/kg | |
| --- | --- | --- | --- | --- |
| | Santos | Sao Paulo | Ghana | Uganda |
| Caffeoylquinic acids (CQA) | 60.8-62.6 | 56.2-58.2 | 79.2-84.3 | 77.1-80.9 |
| Total chlorogenic acids (tCGA) | 64.2-64.8 | 56.5-59.1 | 92.6-94.7 | 83.9-86.6 |

Clifford M N and Wright J, 1976

The torrefaction process has the aim of developing the coffee aroma. The traditional roasting method lasts between 15 and 23 minutes depending on the machinery. The coffee beans are gradually heated while being constantly tossed about. At about 100° C., the beans go yellowish and lose a good proportion of their water by evaporation. Towards 150° C., the beans that have become light brown begin to give off an aroma. Between about 200 and 250° C., the beans become a mahogany brown color. If the torrefaction is continued (230° C.), the bean becomes quite black. This change of color is known as the Stucker reaction. Under the effect of heat, certain constituents disappear; others combine with each other to form complex products. In the first 10 minutes, caramelization of sugars occurs from 160° C.: this is known as Maillard's reaction. At the end of about 10 minutes (200° C.), this reaction causes the first 4 aromas to arise from aroma precursor acids. These aromas are destroyed by possible carbonization. After 10 minutes, the bean will have lost most of its water by evaporation. The sugars and tannins gradually disappear. During the torrefaction process, the total chlorogenic acids are partially destroyed. Table 3 shows the destruction of chlorogenic acids as a consequence of the torrefaction process of the coffee. Therefore, it is desirable to avoid the roasting process in order to preserve a high content of chlorogenic acids in the coffee beans.

TABLE 3

Effects of the torrefaction process over the total
chlorogenic acids (tCGA) in the green coffee.

| Green coffee beans | Total chlorogenic acids (tCGA) | Torrefaction (205° C.) | | | |
| --- | --- | --- | --- | --- | --- |
| | | Soft (7 min) | Mild | Strong (13 min) | Really strong (19 min) |
| *Coffea Arabica* (Guatemala) | 57.6 | 23.8 | 19.8 | 7.1 | 2.2 |
| *Coffea robusta* (Uganda) | 68.2 | 30.2 | 17.8 | 5.2 | 1.4 |

Trugo and Macrae, 1984

Studies managed by the NAT'Life Division of Naturex and INRA (National Institute of Agronomic Research) allowed to clarify chlorogenic acids absorption thanks to in situ stomach infusion, intestinal perfusion models and nutritional intervention experiment in rats. Different absorption sites and different metabolites were identified. The results showed that about 30% of chlorogenic acids are absorbed from the stomach and the small intestine, the other part reaching the colon (FIG. 1). From the stomach, the absorption does not induce modifications in the CGA structures. The absorption in the stomach represents about 16% of the total ingested. From the small intestine and the colon, most of the chlorogenic acids ingested are hydrolysed into caffeic and quinic acids. In the small intestine, chlorogenic acids are hydrolysed by enterocytes. The caffeic acid next liberated is O-methylated. After that, caffeic and (iso)ferulic acids go to the blood and can be metabolized in the tissues. In the colon, chlorogenic acids are hydrolyzed by the microflora. Quinic and caffeic acids are thus released, directly absorbed and metabolized by enterocytes, metabolized by the intestinal flora, absorbed and metabolized again by colonocytes and finally excreted in the feces.

It has been demonstrated that tCGA regulates glycemia by inhibiting glucose-6-phosphatase (Glc-6-Pase) system activity. Glc-6-Pase plays an important role in the homeostatic control of blood sugar concentration. This enzyme system, only present in the liver, is in fact responsible for the conversion of glucose-6-phosphate into glucose which is then capable of passing into the general circulation. Inhibition of hepatic Glc-6-Pase causes a reduction in the hepatic production of glucose and consequently decreases abnormally high levels of glucose in the blood.

Recent discoveries have shown that 5-caffeoylquinic acid (5-CQA) inhibits the activity of Glc-6-Pase in a specific way, in particular the activity of its Glc-6-Pase translocase 1 unit (T1) (McCarty. *Med Hypotheses*. 2001 March; 56 (3): 286-289). In vitro and in vivo studies carried out with 5-CQA, the main polyphenol in coffee, showed that this phenolic acid is able to modulate glucose metabolism (Welsch et al. *J. Nutr.*, 1989. 119 (11):1698-1704.—Anion et al. *Arch Biochem Biophys*, 1997. 339 (2):315-22.—Herling et al. *Am J Physiol*, 1998. 274 (6 Pt 1): p. G1087-93. —Hsu et al. *Planta Med*, 2000. 66 (3): p. 228-30.—Andrade-Cetto et al. *J Ethnopharmacol*, 2001. 78 (2-3): p. 145-9. —Rodriguez de Sotillo et al. *JNutr Biochem*, 2002. 13 (12): p. 717-726.—Johnston et al. *Am J Clin Nutr*, 2003. 78 (4): p. 728-33). More particularly, it was shown that 5-CQA inhibits Glc-6-Pase in intact rat microsomes while no effect was shown in fully disrupted microsomes. However, there is no evidence for the inhibition of Glc-6-Pase by other CGAs nor by green coffee extract.

Blum et al. (*Nutrafoods* 2007; 6 (3):13-17.) conducted a study in order to determine the hypoglycaemic effect of a green coffee extract (Svetol® green coffee extract, NATUREX) in humans. The aim of the clinical trial was to determine if the green coffee extract could decrease glycemia in the postprandial state in humans. Fifteen healthy women (18-70 y) participated in the study. All participants were used as their own control and were submitted to an oral glucose tolerance test before and after supplementation of the green coffee extract. The supplementation consisted of 600 mg of green coffee extract daily during forty days, divided in three doses of 200 mg each before the meals. Results indicated a significant decrease (147±9.3 vs 133±8.7 mg/dL; p<0.05) in post-load glycemia compared to the one obtained before supplementation (FIG. 2). Moreover at the end of the study, a weight loss of around 1.5 kg was noted. In conclusion, these preliminary results suggest that green coffee extract is able to modulate glucose metabolism and that this modulation could have an effect on weight management.

In another clinical trial, Deallalibera et al. (*Phytotherapie experimentale* 2006 November; 4 (4):194-197) studied the effect of a green coffee extract (Svetol® green coffee extract, NATUREX) on body weight loss in humans. Fifty overweight volunteers (BMI>25 kg/m$^2$) were randomized in two groups, control group (n=20) receiving placebo, and treated group (n=30) receiving the green coffee extract (Svetol® green coffee extract, NATUREX) with bland low calorie diet. Each volunteer took one capsule of the 200 mg of green coffee extract twice a day with the main meal, for 60 days. Changes in Muscle Mass/Fat Mass ratio (MM/FM), body weight, body mass index (BMI), and self evaluation of physical aspects were recorded at baseline and at the end of the study. After 60 days, the MM/FM ratio was increased statistically in the green coffee group compared to the placebo: 4.1±0.7% vs. 1.6±0.6% respectively (P<0.01). Moreover, a significant reduction in weight of 4.97±0.32 kg (5.7%), as well as in the BMI (−1.7 kg/m$^2$), were observed in the green coffee extract compared to the placebo (P<0.001). The significant increase of MM/FM ratio and decrease of weight and BMI showed that the green coffee extract (Svetol® green coffee extract, NATUREX) is able to exacerbate effect of a bland low calorie diets on volunteers who are overweight. This effect could be explained by increasing the consumption of fatty deposits and by preventing them from being accumulated.

SUMMARY OF THE INVENTION

Broadly, the present invention is directed to methods of using green coffee extract, such as Svetol® brand green coffee extract (commercially available from NATUREX S.A., Avignon France), to inhibit the Glc-6-Pase system, reduce glycemia and promote reduced body fat, increase Muscle Mass/Fat Mass ratio (MM/FM) in the body, and reduce the body weight and body mass index (BMI) in humans. One aspect of the invention is directed to a method of improving body weight in humans and reducing the risk of Type 2 diabetes (T2D) by administering an amount of green coffee extract effective to treat a subject. A preferred green coffee extract contains a ratio of 5-caffeoylquinic acid (5-CQA) to total chlorogenic acids (tCGA) (5-CQA/tCGA) of from about 0.2 and 0.3. More preferably, the concentration of tCGA is greater than about 45% and the concentration of 5-CQA is less than about 10%. A preferred method of administration consists of administering between about 200 mg and about 1,000 mg per day, more preferably administering about 400 mg per day. In one embodiment, the green coffee extract is administered to a subject in a dosage of between about 200 mg and about 1,000 mg per day of green coffee extract.

The green coffee extract from *Coffea robusta* beans is preferably obtained by hydroalcoholic extraction with a plant/extract ratio of between 6:1 and 8:1. The alcohol solvent used is exclusively food quality alcohol. Preferably, the green coffee extract, although rich in tCGA and 5-CQA, contains no caffeine. In addition, the choice of raw material and the extraction conditions provide an extract containing no cafestol or kahweol, constituents of coffee which can increase the risk of cardiovascular disease.

The inventors believe they are the first to have discovered that one can use a green coffee extract for the inhibition of the Glc-6-Pase system. The inhibition of the Glc-6-Pase system is favored by the ratio existing between 5-CQA and tCGA in the green coffee extract. For the first time, it is demonstrated that not only 5-CQA inhibits the Glc-6-Pase system, but also other CGA present in the green coffee extract. This specially designed green coffee extract is more effective in inhibiting the Glc-6-Pase system than the combination of isolated CGA, evidencing a greater level of synergy between all natural CGA present in the extract.

The inventors also believe that the inhibition of Glc-6-Pase system is favored by the presence of 5-CQA, 4-CQA, 3,4-diCQA and 4,5-diCQA in the green coffee extract. In some embodiments, the green coffee extract comprises from about 6% to about 8% of 4-caffeoylquinic acid; from about 13% to about 16% of 5-caffeoylquinic acid; 3.57% of 3,4-dicaffeoylquinic acid±a standard deviation of 0.54%; and 4.22% of 4,5-dicaffeoylquinic acid±a standard deviation of 0.15%, by weight of the green coffee extract.

In one embodiment of the invention, the bioavailability of CGA in humans is defined from the specially designed green coffee extract of the present invention. Data on the bioavailability of CGA from green coffee in humans was previously nonexistent. The special composition in the green coffee extract allows that three CQA, three diCQA and caffeic, ferulic, isoferulic and p-coumaric acids are bioavailable in plasma; and 4-CQA, 5-CQA and sinapic, p-hydroxybenzoic, gallic, vanillic, dihydrocaffeic, caffeic, ferulic, isoferulic, and p-coumaric acids in urine. Therefore, the CGA in the green coffee extract, which is also able to inhibit the Glc-6-Pase system activity, is bioavailable in humans as evidenced in plasma and urine.

In another embodiment of the invention, a green coffee extract (Svetol® green coffee extract, NATUREX) is applied and able to reduce glycemia in humans.

In another embodiment of the invention, a green coffee extract (Svetol® green coffee extract, NATUREX) is applied and able to reduce body fat in humans.

In another embodiment of the invention, a green coffee extract (Svetol® green coffee extract, NATUREX) is applied and able to increase the Muscle Mass/Fat Mass ratio (MM/FM) in humans.

In another embodiment of the invention, a green coffee extract (Svetol® green coffee extract, NATUREX) is applied and able to reduce body weight in humans.

In a further embodiment of the invention, a green coffee extract (Svetol® green coffee extract, NATUREX) is applied and able to reduce Body Mass Index (BMI) in humans.

BRIEF DESCRIPTION OF THE FIGURES

Further features, advantages and characteristics of the present invention will become apparent to a person of ordinary skill in the art in view of the following detailed discussion of preferred embodiments of the present invention, made with reference to the drawings annexed, in which.

DESCRIPTION OF THE INVENTION

Figure 1:
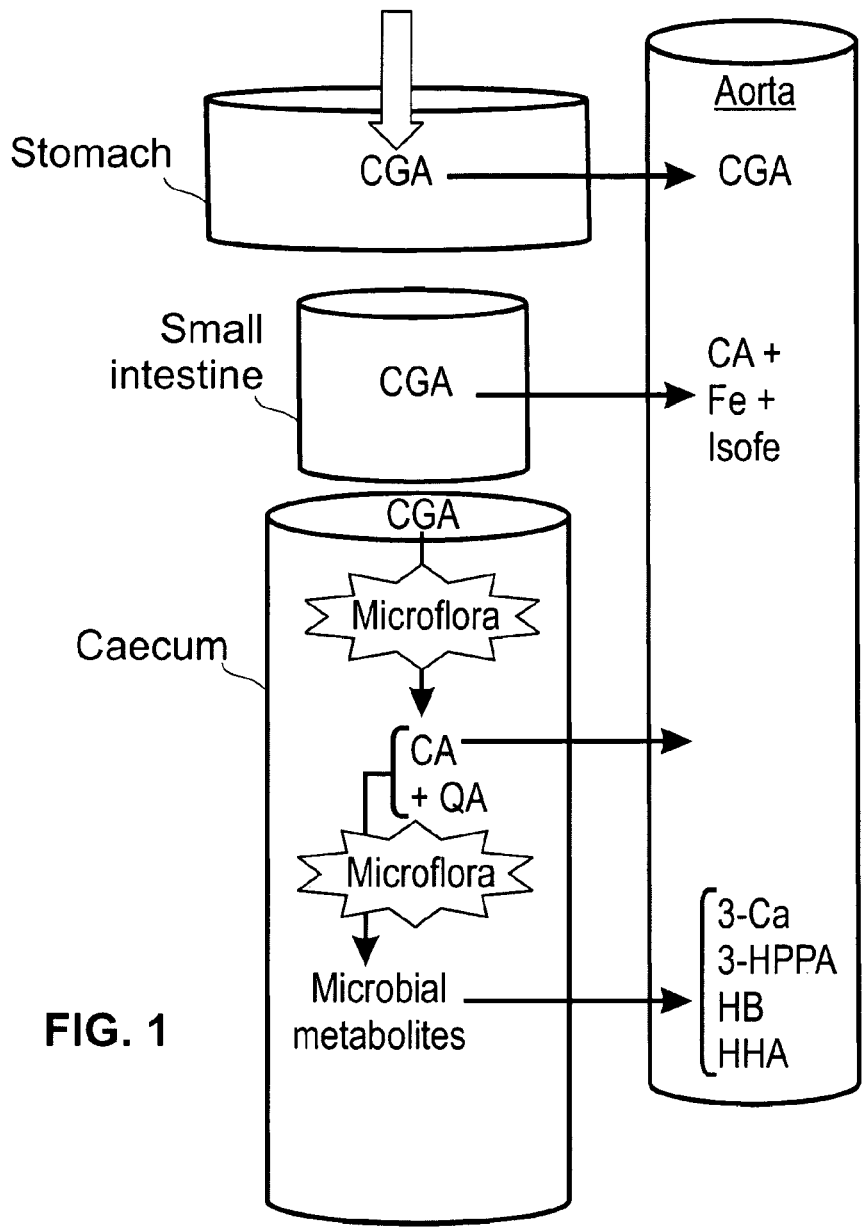
FIG. 1 provides a diagram summarizing chlorogenic acids absorption.
Figure 2:
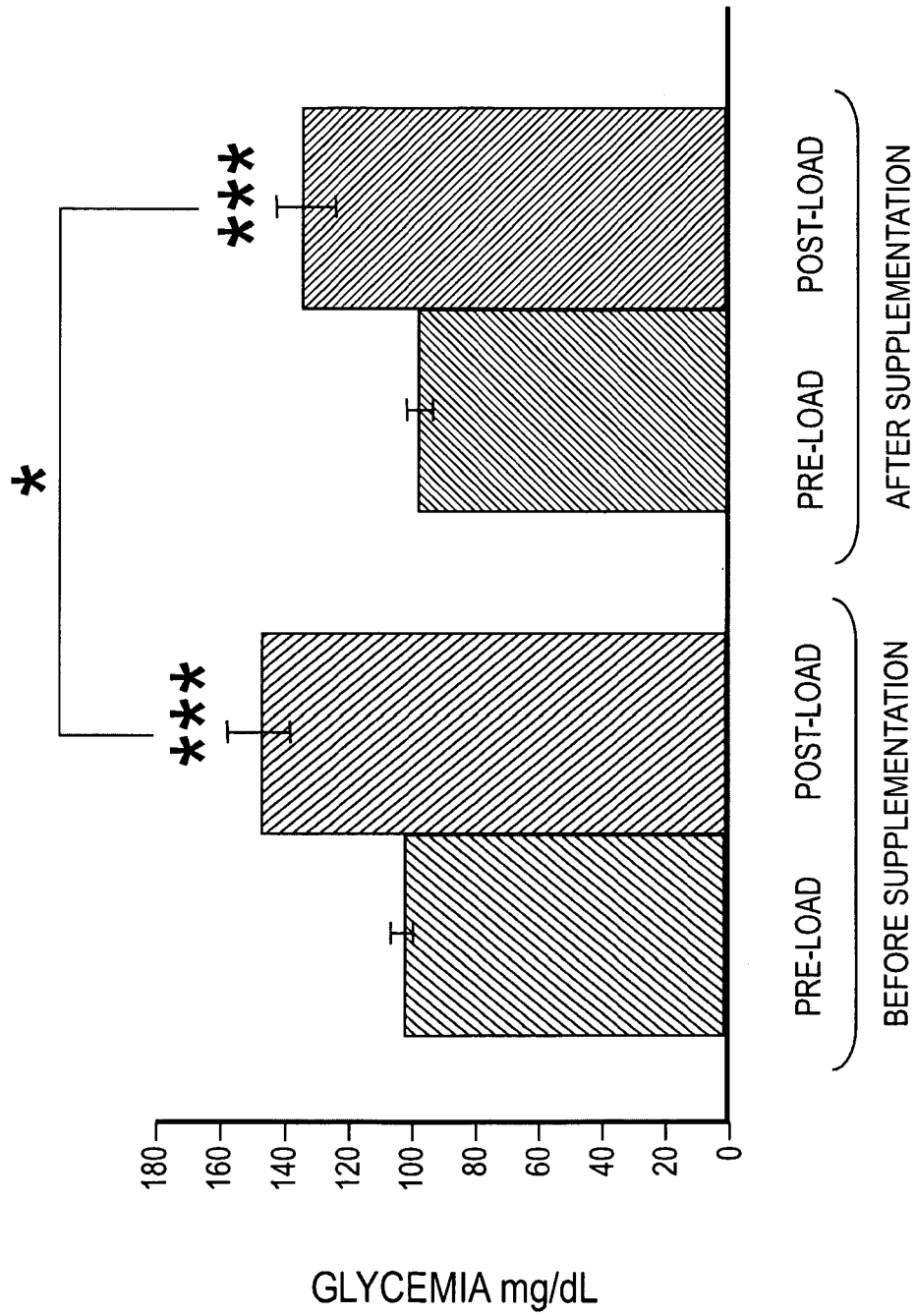
FIG. 2 illustrates an oral glucose tolerance test with and without green coffee extract (Svetol® green coffee extract, NATUREX) supplementation.
Figure 3:
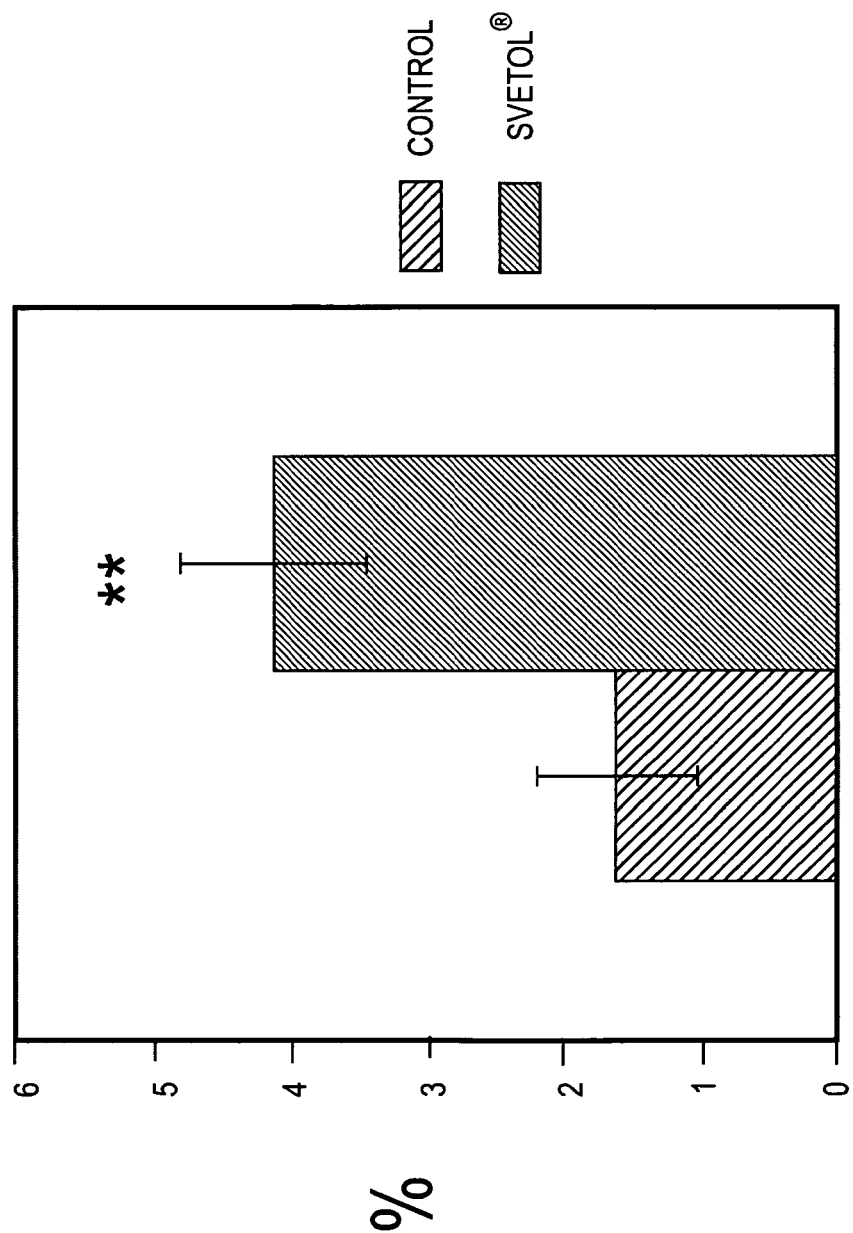
FIG. 3 illustrates the variation (%) of the Muscle Mass/Fat Mass ratio (MM/FM) after 60 days of green coffee extract (Svetol® green coffee extract, NATUREX) supplementation. **P<0.01.
Figure 4:
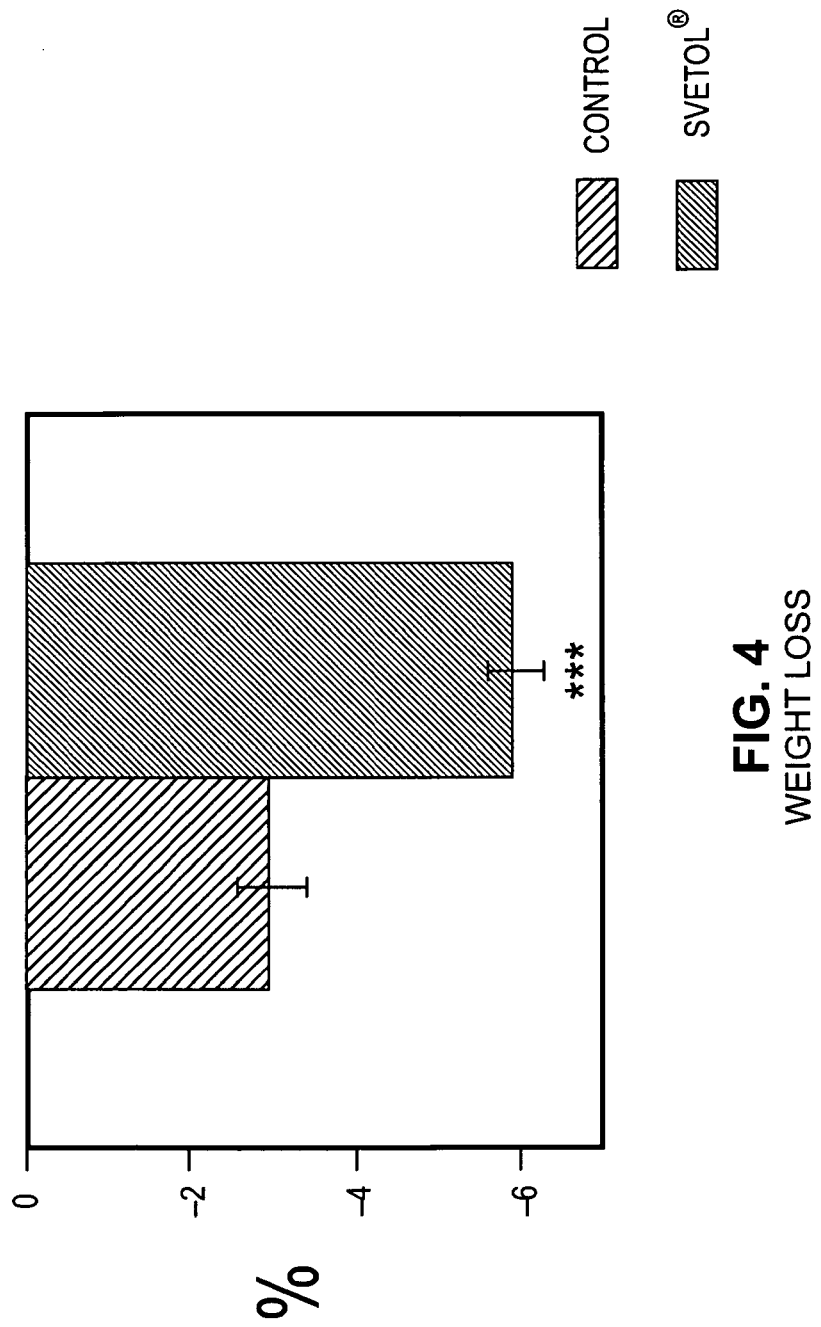
FIG. 4. Weight loss reduction after 60 days of green coffee extract (Svetol® green coffee extract, NATUREX) supplementation. **P<0.001.
Figure 5:
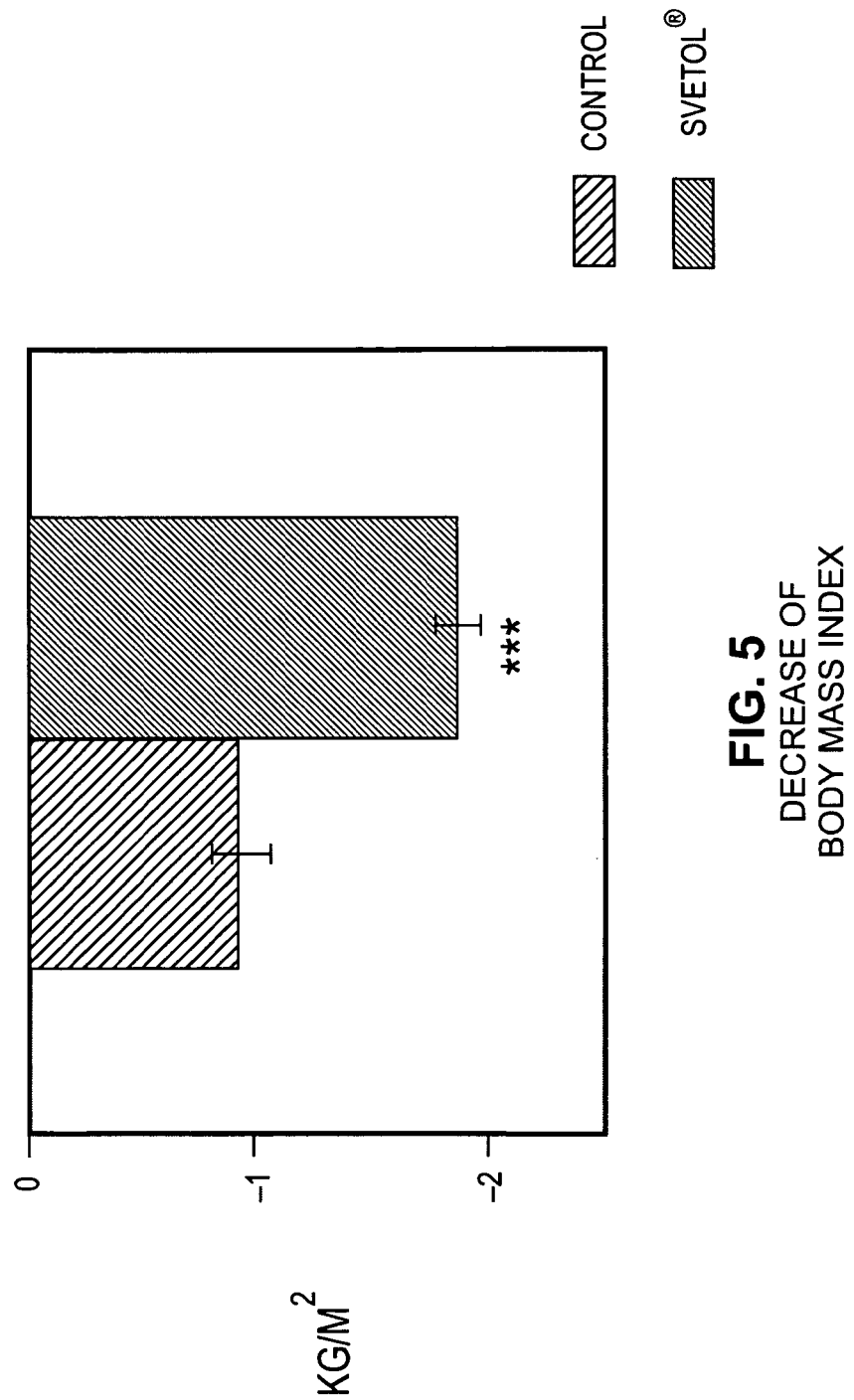
FIG. 5 illustrates Body Mass Index (BMI) reduction after 60 days of green coffee extract (Svetol® green coffee extract, NATUREX) supplementation. **P<0.001.

With reference to the drawings, the present invention related to methods of using green coffee extract, such as Svetol® green coffee extract (NATUREX), to, among other things, inhibit Glc-6-Pase system, reduce glycemia, reduce body fat, increase the Muscle Mass/Fat Mass ratio (MM/FM) in the body, and reduce the body weight and body mass index (BMI) in humans, as will now be described through the following examples. As noted, in a preferred embodiment, the green coffee extract from *Coffea robusta* beans is obtained by hydroalcoholic extraction with a plant/extract ratio of between 6:1 and 8:1. The alcohol solvent used is exclusively food quality alcohol.

In preferred embodiments, the green coffee extract exceeds about 45% of total chlorogenic acids (tCGA), by weight of the green coffee extract. The green coffee extract, in some embodiments, comprises from about 6% to about 8%, by weight of the green coffee extract, of 4-caffeoylquinic acid. The green coffee extract, in some embodiments, comprises exceeding about 10% of 5-caffeoylquinic acid. In some embodiments, the green coffee extract comprises from about 6% to about 8% of 4-caffeoylquinic acid; from about 13% to about 16% of 5-caffeoylquinic acid; 3.57% of 3,4-dicaffeoylquinic acid±a standard deviation of 0.54%; and 4.22% of 4,5-dicaffeoylquinic acid±a standard deviation of 0.15%, by weight of the green coffee extract.

In a preferred embodiment, the green coffee extract comprises from about 5% to about 8% of 3-caffeoylquinic acid; from about 6% to about 8% of 4-caffeoylquinic acid; from about 13% to about 16% of 5-caffeoylquinic acid; 3.57% of 3,4-dicaffeoylquinic acid±a standard deviation of 0.54%; 2.38% of 3,5-dicaffeoylquinic acid±a standard deviation of 0.08%; 4.22% of 4,5-dicaffeoylquinic acid±a standard deviation of 0.15%; from about 1% to about 2% of 3-feruloylquinic acid; from about 1% to 2% of 4-feruloylquinic acid; from about 3% to about 4% of 5-feruloylquinic acid; from about 0.6% to about 0.8% of 3,4-caffeoylferuloylquinic acid; from about 0.2% to about 0.4% of 3,5-caffeoylferuloylquinic acid; from about 0.1% to 0.6% of 4,5-caffeoylferuloylquinic acid; and from about 0.2% to about 1.8% of caffeoyltryptophan, all by weight of the green coffee extract.

In some embodiments, the green coffee extract comprises a ratio of 4-caffeoylquinic acid (4-CQA) to total chlorogenic acids (tCGA) (4-CQA/tCGA) of from about 0.1 to about 0.2. The green coffee extract, in some embodiments, comprises a ratio of 5-caffeoylquinic acid (5-CQA) to total chlorogenic acids (tCGA) (5-CQA/tCGA) of from about 0.2 to about 0.3.

The green coffee extract, in some embodiments, comprises additional ingredients selected from the group consisting of amino acids; caffeine; excipients; extracts; minerals; vitamins; and mixtures thereof. The amino acids comprise those selected from the group of 1-carnitine; 1-leucine; 1-glutamine; 1-almandine; glycine; and mixtures thereof. Preferably, the green coffee extract comprises 1-carnitine. In some embodiments, the green coffee—although rich in tCGA and 5-CQA—contains no caffeine, cafestol or kahweol. In some embodiments, the green coffee extract excipients comprise those selected from the group of starch; microcrystalline cellulose; silicon dioxide; magnesium stearate; and mixtures thereof. Extracts comprise those selected from the group consisting of tea leaf; guarana seed; yerba mate leaf; cinnamon bark; banana leaf; *capsicum* fruit; and mixtures thereof. Minerals can comprise those selected from calcium, magnesium, chromium and mixtures thereof. In one embodiment, the green coffee extract comprises vitamins selected from the group consisting of Vitamin A; Vitamin D; Vitamin C Ascorbic; Vitamin C Ester; Vitamin B Complex; Vitamin E; and mixtures thereof. In a preferred embodiment, the green coffee extract further comprises vitamins selected from the group consisting of Vitamin C Ascorbic, Vitamin C Ester, Vitamin E and mixtures thereof.

The green coffee extract, in some embodiments, can be administered to a subject in the form selected from the group consisting of liquid; semi-liquid; gel; suspensions; capsules; caplets; tablets; and mixtures thereof. In some embodiments, the green coffee extract is administered in a dose of between about 200 mg and 1,000 mg per day. In preferred embodiments, the green coffee extract is administered in a dose of 400 mg per day. In some embodiments, the green coffee extract is administered in a dose of about 200 mg twice a day. In some embodiments, the green coffee extract is administered a dose on an empty stomach prior to two meals. The green coffee extract, in some embodiments, is administered for a 60-day period.

EXAMPLES

Example 1

In some embodiments, the green coffee extract comprises, Nutritional profiles of a green coffee extract (Svetol® green coffee extract, NATUREX). Nutritional analyses were conducted according to the European pharmacopoeia. Table 4 shows the nutritional value of the green coffee extract used in the examples reported herein (Svetol® green coffee extract, NATUREX).

TABLE 4

Nutritional profile of the green coffee extract (Svetol ® green coffee extract, NATUREX).

| Compound | Concentration |
| --- | --- |
| Loss of drying [JO Mar. 11, 1977] | 5% |
| Proteins (Nx6.25) [JO Mar. 11, 1977] | 9% |
| Lipids [JO Mar. 11, 1977] | 1% |
| Ash [JO Mar. 11, 1977] | 10% |
| Soluble sugars [JO Mar. 11, 1977] | 24% |

TABLE 4-continued

Nutritional profile of the green coffee extract (Svetol ® green coffee extract, NATUREX).

| Compound | Concentration |
| --- | --- |
| Caffeine [HPLC] | 1% |
| Total polyphenols [Folin-Ciocalteau] | 50% |
| (tCGA) Total chlorogenic acids [HPLC] | 45% |
| (5 CQA) 5-caffeoylquinic acid [HPLC] | >10% |
| Cafestol [HPLC] | <2 ppm |
| Kahweol [HPLC] | <2 ppm |
| TOTAL | 100% |

The ratio between 5-caffeoylquinic acid (5-CQA) and total chlorogenic acids (tCGA) (5-CQA/tCGA in Table 4) of the green coffee extract (Svetol® green coffee extract, NATUREX) is between 0.2 and 0.3.

Example 2

HPLC Chromatogram of the Green Coffee Extract (Svetol® Green Coffee Extract, NATUREX)

Figure 6:
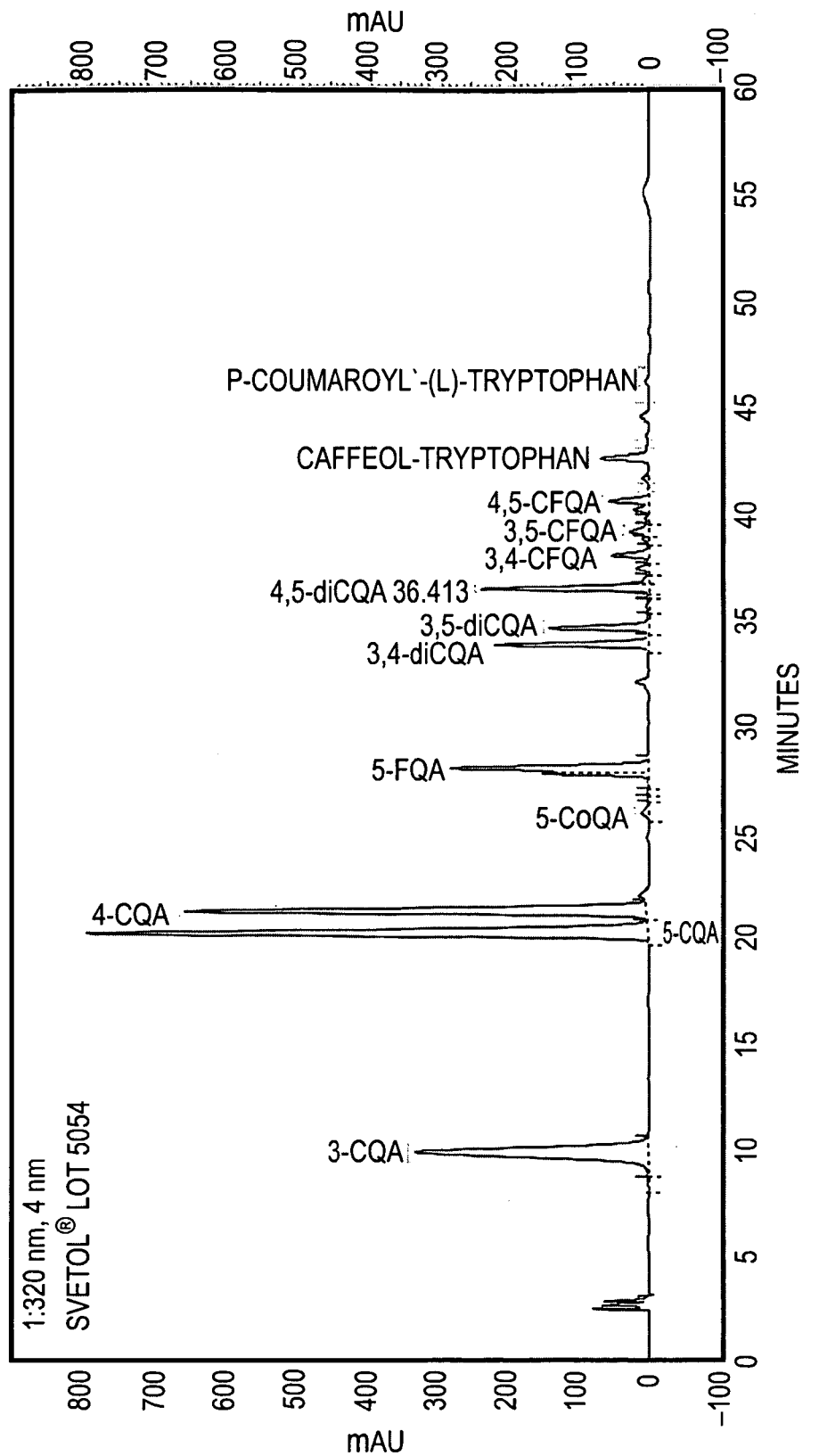
FIG. 6 provides the high-pressure liquid chromatography chemical fingerprint for a green coffee extract (Svetol® green coffee extract, NATUREX)

The high-pressure liquid chromatography chemical fingerprint for a green coffee extract (Svetol® green coffee extract, NATUREX) is presented in FIG. 6. The method for performing this analysis was as follows: HPLC-DAD was achieved using a column RP-$C_{18}$ (5 µm-250×4.6 mm) at 55° C. The flow rate was 0.8 mL/min, and the elution was monitored at 330 nm. The mobile phases were (A) distilled water+$H_3PO_4$ 0.002M, and (B) acetonitrile. A solution of 100% A was maintained during 8 min, increased by linear gradient to 35% A and 65% B by volume after 35 min total time; followed by a linear gradient of 100% A after maintaining this composition for 10 min; the system was then re-equilibrated to the initial composition. The content of CGA from 10 batches of green coffee extract (Svetol® green coffee extract, NATUREX) reported as mean±standard deviation (SD) is shown in Table 5.

TABLE 5

Chlorogenic acids (CGA) of the green coffee extract (Svetol ® green coffee extract, NATUREX).

| Compound | Concentration % | Standard Deviation |
| --- | --- | --- |
| 3-caffeoylquinic acid (3-CQA) | 8.91 | 0.71 |
| 4-caffeoylquinic acid (4-CQA) | 10.47 | 0.74 |
| 5-caffeoylquinic acid (5-CQA) | 12.55 | 0.84 |
| 4-feruloylquinic acid (4-FQA) | 0.00 | 0.00 |
| 5-feruloylquinic acid (5-FQA) | 4.47 | 0.18 |
| 3,4-caffeoylferuloylquinic acid (3,4-diCQA) | 2.63 | 0.15 |
| 3,5-caffeoylferuloylquinic acid (3,5-diCQA) | 1.72 | 0.14 |
| 4,5-caffeoylferuloylquinic acid (4,5-diCQA) | 2.90 | 0.22 |
| 3,4-caffeoylferuloylquinic acid (3,4-CFQA) | 0.62 | 0.02 |
| 3,5-caffeoylferuloylquinic acid (3,5-CFQA) | 0.18 | 0.16 |
| 4,5-caffeoylferuloylquinic acid (4,5-CFQA) | 0.66 | 0.03 |
| 5-Coumaroylquinic acid (5-CoQA) | 0.18 | 0.02 |
| Caffeic acid | 0.00 | 0.00 |
| Caffeoyl-tryptophan | 0.99 | 0.09 |
| p-coumaroyl-tryptophan | 0.13 | 0.04 |
| Total | 46.41 | 1.35 |

Example 3

Composition of Total Chlorogenic Acids (tCGA) and 5-Caffeoylquinic Acid (5-CQA) in Several Coffee Extracts Table 6 shows the composition of chlorogenic acids (tCGA) and 5-caffeoylquinic acid (5-CQA), as well as the ratio 5-CQA/tCGA, of several commercial extracts. All samples were analyzed using the HPLC method described in Example 2. The last two rows include the values of the green coffee extract described in this invention (Svetol® green coffee extract, NATUREX).

TABLE 6

Composition of total chlorogenic acids (tCGA) and 5-caffeoylquinic acid (5-CQA) in several coffee extracts

| Coffee extract | tCGA (HPLC) | 5-CQA | Ratio 5-CQA/ tCGA | Specie |
|---|---|---|---|---|
| Svetol ®, Naturex [1] | 46.41 | 12.55 | 0.27 | C. robusta |
| Commercial sample 1 | 5.57 | 2.2 | 0.39 | C. arabica |
| Commercial sample 2 | 6.07 | 2.2 | 0.36 | C. arabica |
| Commercial sample 3 | 5.55 | 1.98 | 0.36 | C. arabica |
| Commercial sample 4 | 50 | 24 | 0.48 | C. arabica |
| Commercial sample 5 | 35 | 18 | 0.51 | C. arabica |
| Commercial sample 6 | 45 | 19 | 0.42 | C. arabica |
| Commercial sample 7 | 27 | 5 | 0.19 | C. arabica |
| Commercial sample 8 (Batch 1) | 53 | / | | C. arabica |
| Commercial sample 8 (Batch 2) | 45 | 19 | 0.42 | C. arabica |
| Commercial sample 9 (Batch 1) | 79 | 50 | 0.63 | C. arabica |
| Commercial sample 10 | 78 | 59 | 0.76 | C. arabica |
| Commercial sample 11 | 64 | 30 | 0.47 | C. arabica |
| Commercial sample 13 | 79 | 51 | 0.65 | C. robusta |
| Commercial sample 14 | 70.2 | 61.5 | 0.88 | C. robusta |
| Commercial sample 15 | 48 | 21 | 0.44 | C. arabica |
| Commercial sample 16 | 43 | 16 | 0.37 | C. robusta |
| Commercial sample 17 | 66 | | | |

[1] Mean of 10 batches

Example 4

Inhibition of Hepatic Glucose-6-Phosphatase System (Glc-6-Pase System) by Green Coffee Extract (Svetol® Green Coffee Extract, NATUREX)

The aim was to determine if a decaffeinated green coffee extract (Svetol® green coffee extract, NATUREX) is able to inhibit the glucose-6-phophatase (Glc-6-Pase) system and to determine which type of chlorogenic acids, 3-; 4- or 5-caffeoylquinic acids, is the best active molecule.

Glc-6-Pase system activity was assayed by quantifying orthophosphate formation, as described previously (Anion et al. *Arch Biochem Biophys* 1997; 339 (2):315-22). The enzyme assays were conducted in a final rectional volume of 320 μL, containing different concentrations of glucose-6-phosphate ranging from 1 to 20 mM, 100 mM cacodylic acid pH 6.5. The reaction was initiated by the addition of intact or disrupted microsomes, for 5 minutes and was stopped by the addition of 3.2 mL of colorimetric reagent (six volumes of acid molybdate (0.42% ammonium molybdate in 1N $H_2SO_4$), two volumes of 5% SDS and one volume of 10% ascorbic acid, freshly prepared and stored in ice for maximum 6 hours). All samples were then incubated for 30 minutes at 45° C., and the amount of phosphate liberated per minute was determined as the blue phosphomolybdous complex at 820 nm.

Experiments were conducted with or without addition of the green coffee extract (Svetol® green coffee extract, NATUREX) (final concentration of total chlorogenic acids: 0.4 or 0.6 mM) but also with isolated caffeoylquinic acids. The final concentration of pure molecules tested (3-, 4- and 5-caffeoylquinic acids alone or mixed) corresponded to their concentration in green coffee extract tested: 0.08, 0.08, 0.11 and 0.27 mM respectively for the green coffee extract with total chlorogenic acids at 0.4 mM; 0.12, 0.12, 0.17 and 0.41 mM for the green coffee extract with total chlorogenic acids at 0.6 mM. Enzyme activity is expressed as milliunits per milligram of protein. Experiments were conducted in triplicates, and regression analyses of plotted data were carried out using XLStat (Version 2008.1.03, Addinsoft). Comparisons of activities of Glc-6-Pase systems in the presence and absence of the green coffee extract (Svetol® green coffee extract, NATUREX) were performed by one way analysis of variance (ANOVA). The levels of significance was set up at $p<0.05$.

Results of the experiments in disrupted microsomes are shown in FIGS. 7 to 10.

Figure 7:
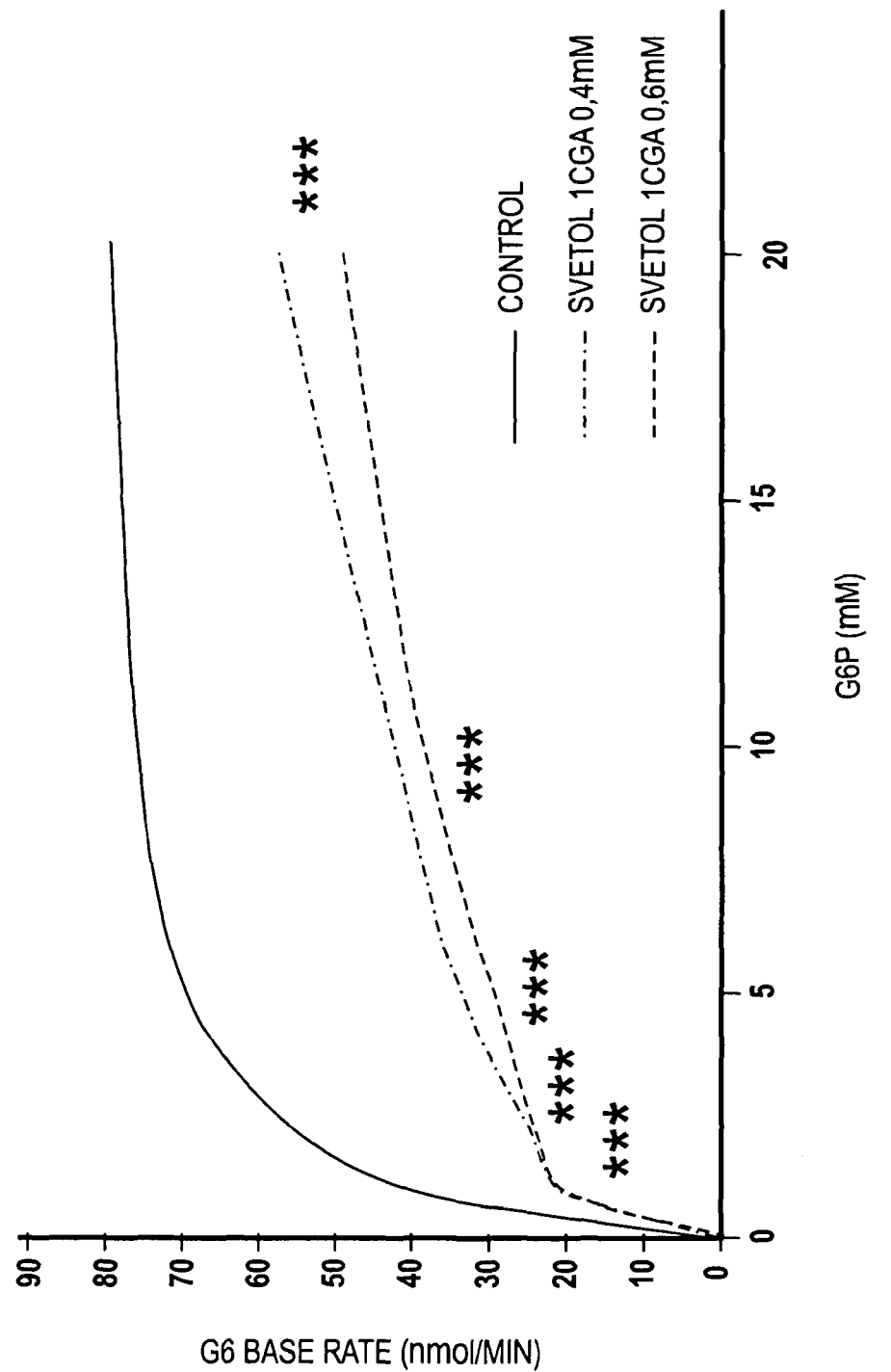
FIG. 7 illustrates the activity of glucose-6-phosphatase in disrupted human microsomes with or without green coffee extract (Svetol® green coffee extract, NATUREX). Values are mean+/−SD. *p<0.05; p<0.01; *p<0.001 vs control.
Figure 8:
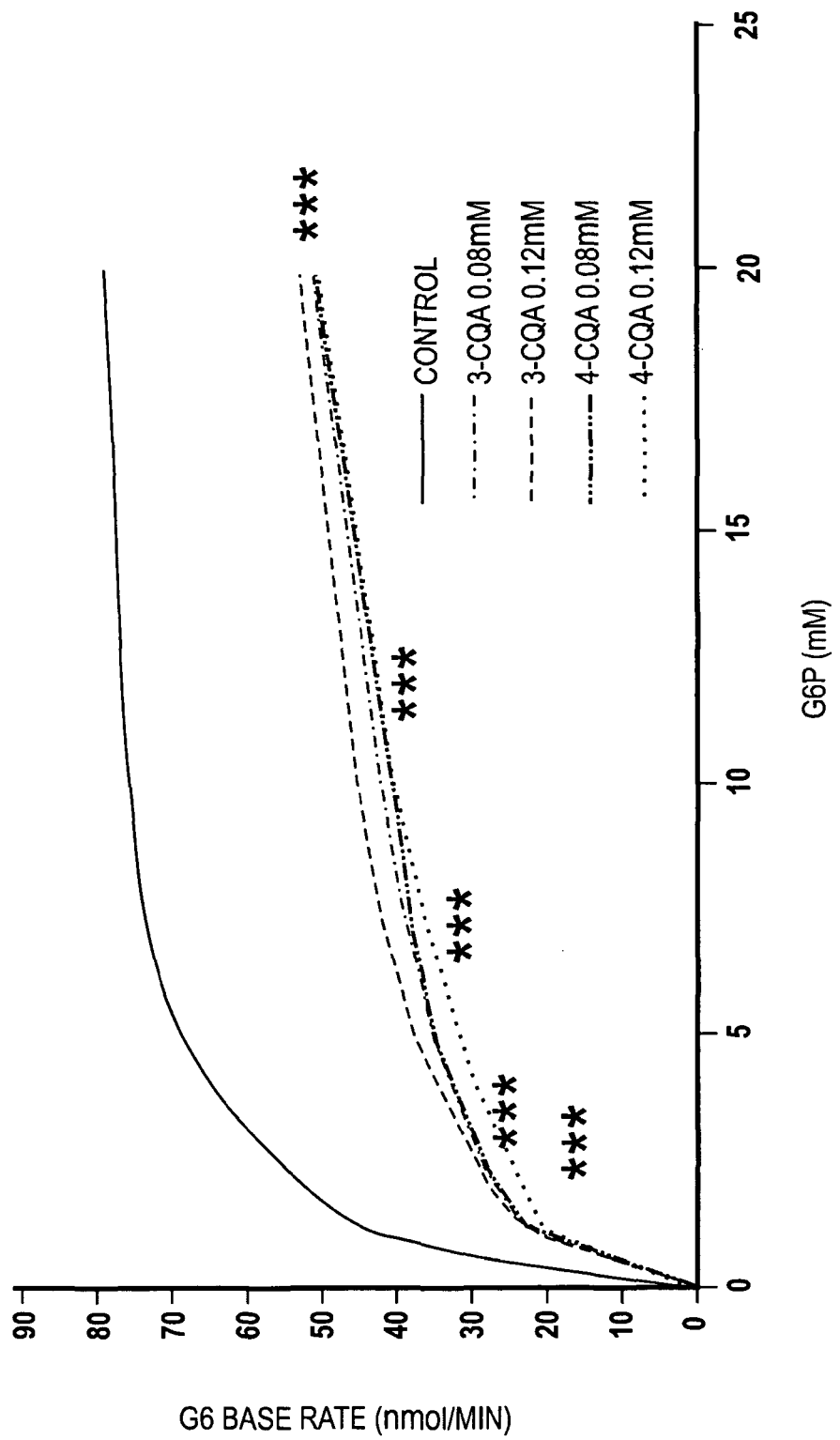
FIG. 8 illustrates the activity of glucose-6-phosphatase in disrupted human microsomes with or without 3-; 4-caffeoylquinic acids tested alone. Values are mean+/−SD. *p<0.05; p<0.01; *p<0.001 vs control.
Figure 9:
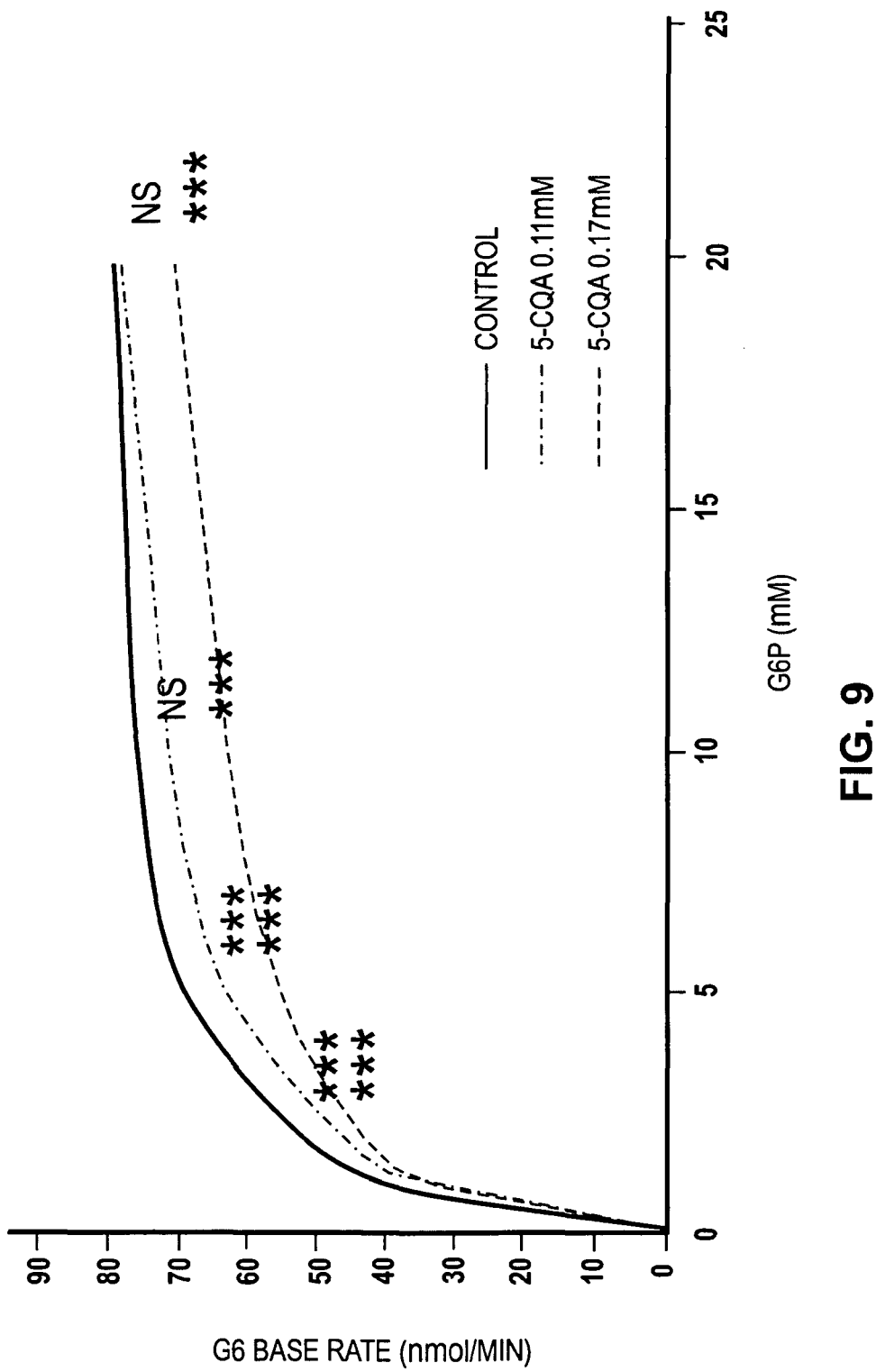
FIG. 9 illustrates the activity of glucose-6-phosphatase in disrupted human microsomes with or without 5-caffeoylquinic acid (5-CQA) tested alone. Values are mean+/−SD. *p<0.05; p<0.01; *p<0.001 vs control.
Figure 10:
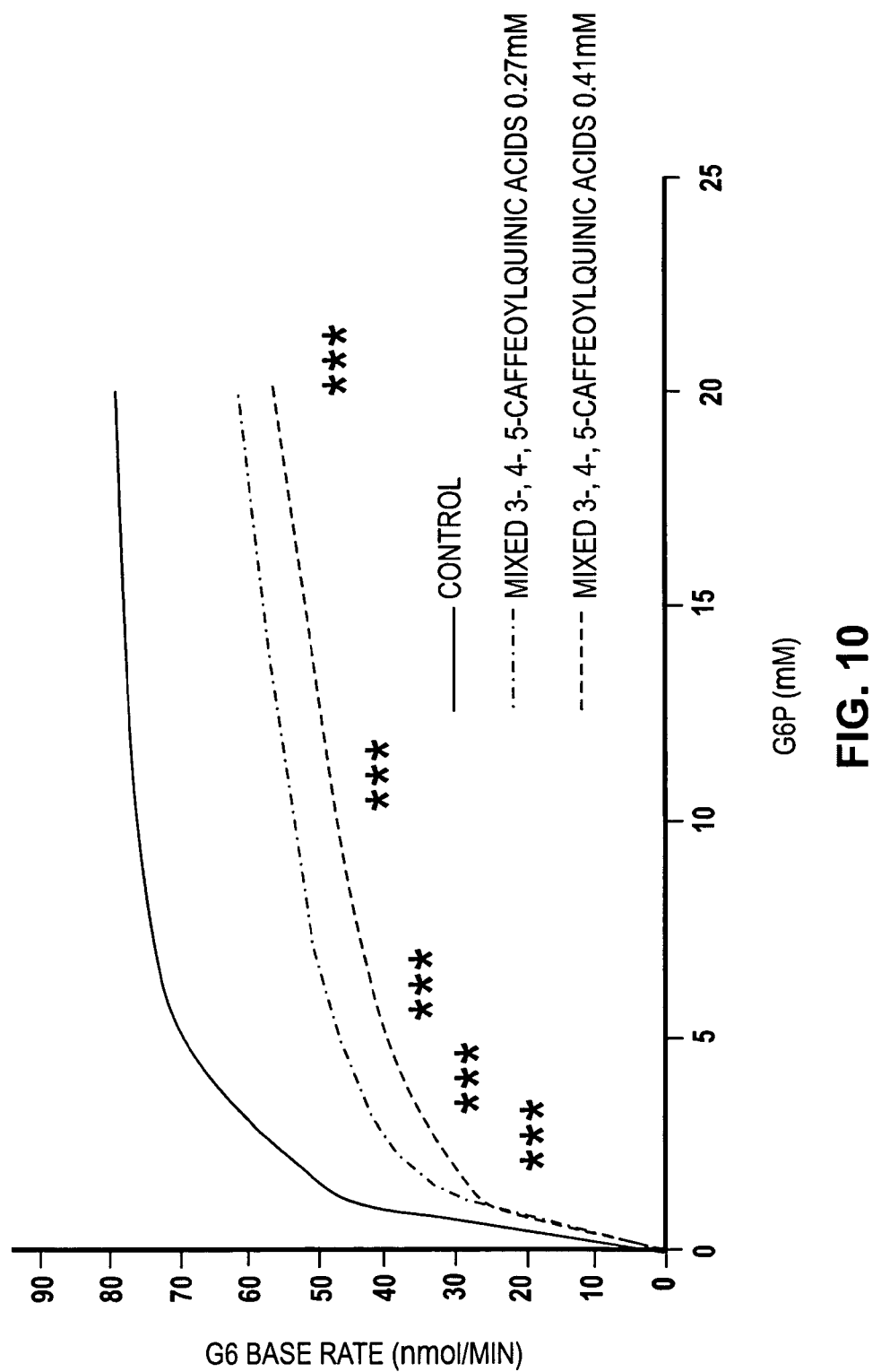
FIG. 10 illustrates the activity of glucose-6-phosphatase in disrupted human microsomes with or without 3-; 4-; 5-caffeoylquinic mixed together. Values are mean+/−SD. *p<0.05; p<0.01; *p<0.001 vs control.

Disrupted microsomes permit to have access directly to the catalytic site. Whatever the concentration of green coffee extract (Svetol® green coffee extract, NATUREX) tested, it inhibits significantly the catalytic site but not in a dose-dependent manner ($p<0.001$ vs control; FIG. 7). When purified chlorogenic acids were tested separately, all of them inhibit significantly the enzyme, however, activities of 3- and 4-caffeoylquinic acids are higher than those of 5-caffeoylqunic acid (FIGS. 8 and 9). When purified chlorogenic acids are mixed together, no synergic effect was shown, the inhibition effect results from the sum of each chlorogenic acid effect independently ($p<0.001$). No dose-dependent effect was shown like the green coffee extract (Svetol® green coffee extract, NATUREX). Moreover the sum of these activities explained a part of the green coffee extract (Svetol® green coffee extract, NATUREX) effect but not the totality suggesting that the caffeoyferuloylquinic acids present in the green coffee extract (Svetol® green coffee extract, NATUREX) are probably also active towards the Glc-6-Pase catalytic site.

Results of the experiments in intact microsomes are shown in FIGS. 11 to 15.

Figure 11:
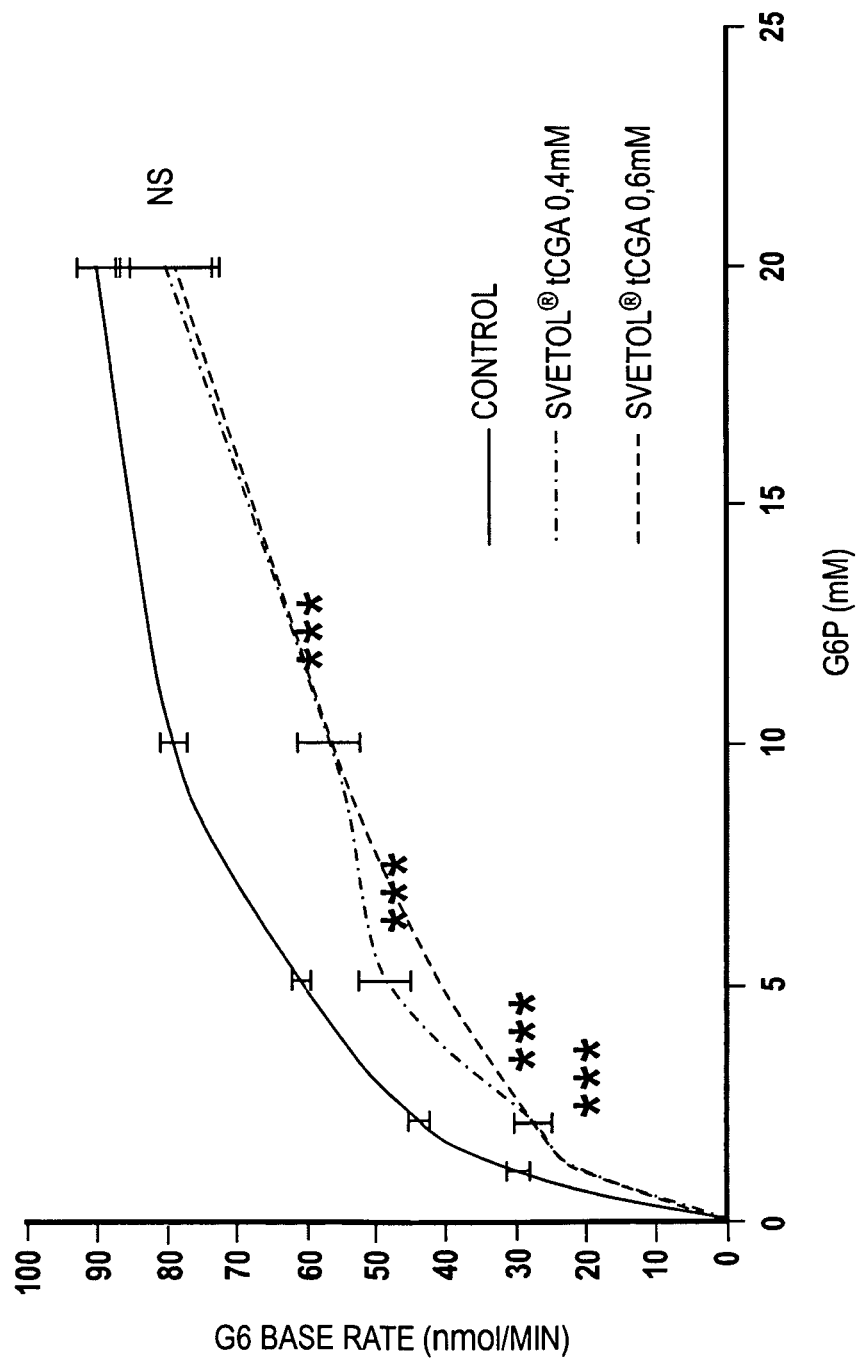
FIG. 11 illustrates the activity of glucose-6-phosphatase in intact human microsomes with or without green coffee extract (Svetol® green coffee extract, NATUREX). Values are mean+/−SD. *p<0.05; p<0.01; *p<0.001 vs control.
Figure 12:
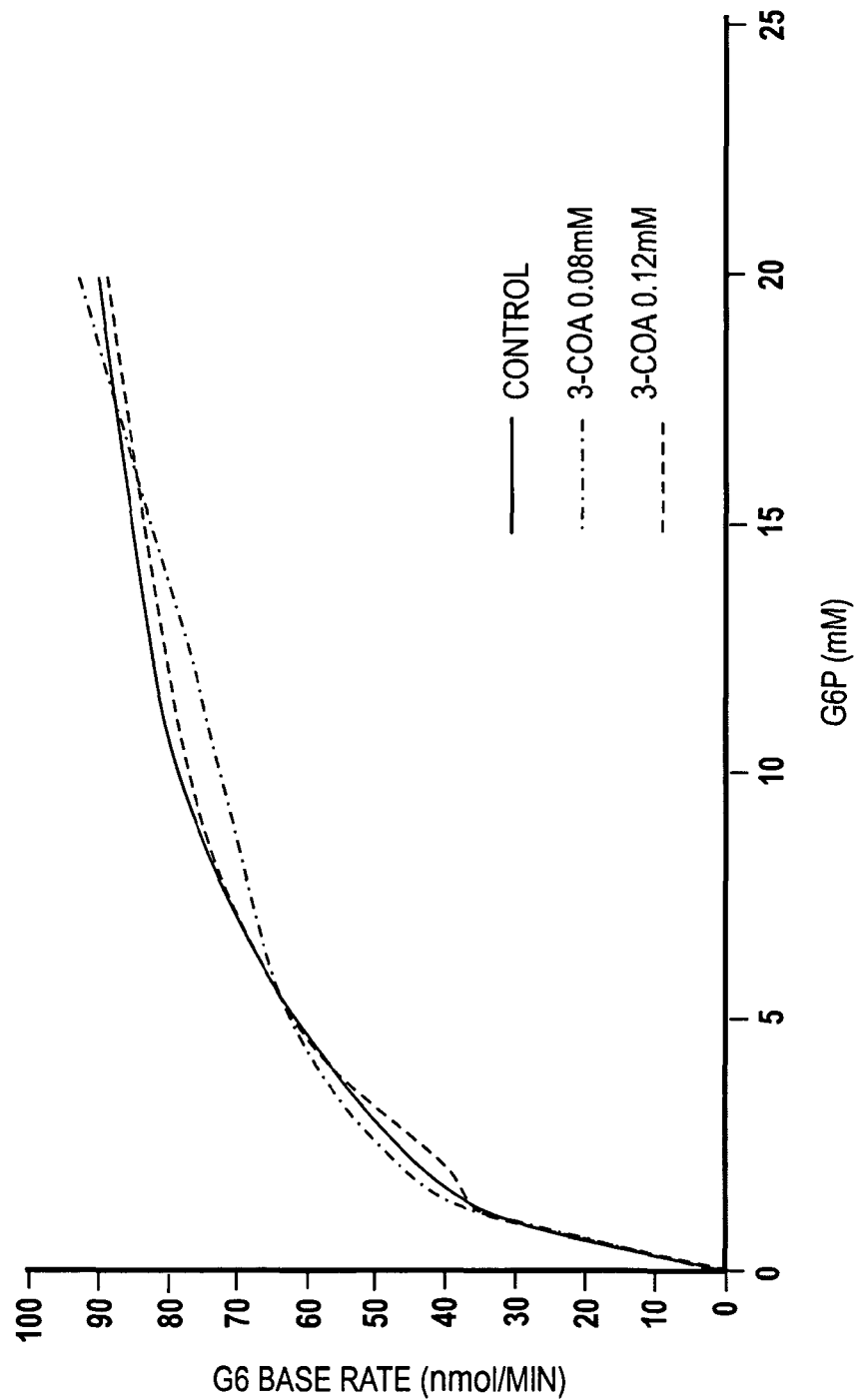
FIG. 12 illustrates the activity of glucose-6-phosphatase in intact human microsomes with or without 3-caffeoylquinic acids tested alone. Values are mean+/−SD. *p<0.05; p<0.01; *p<0.001 vs control.
Figure 13:
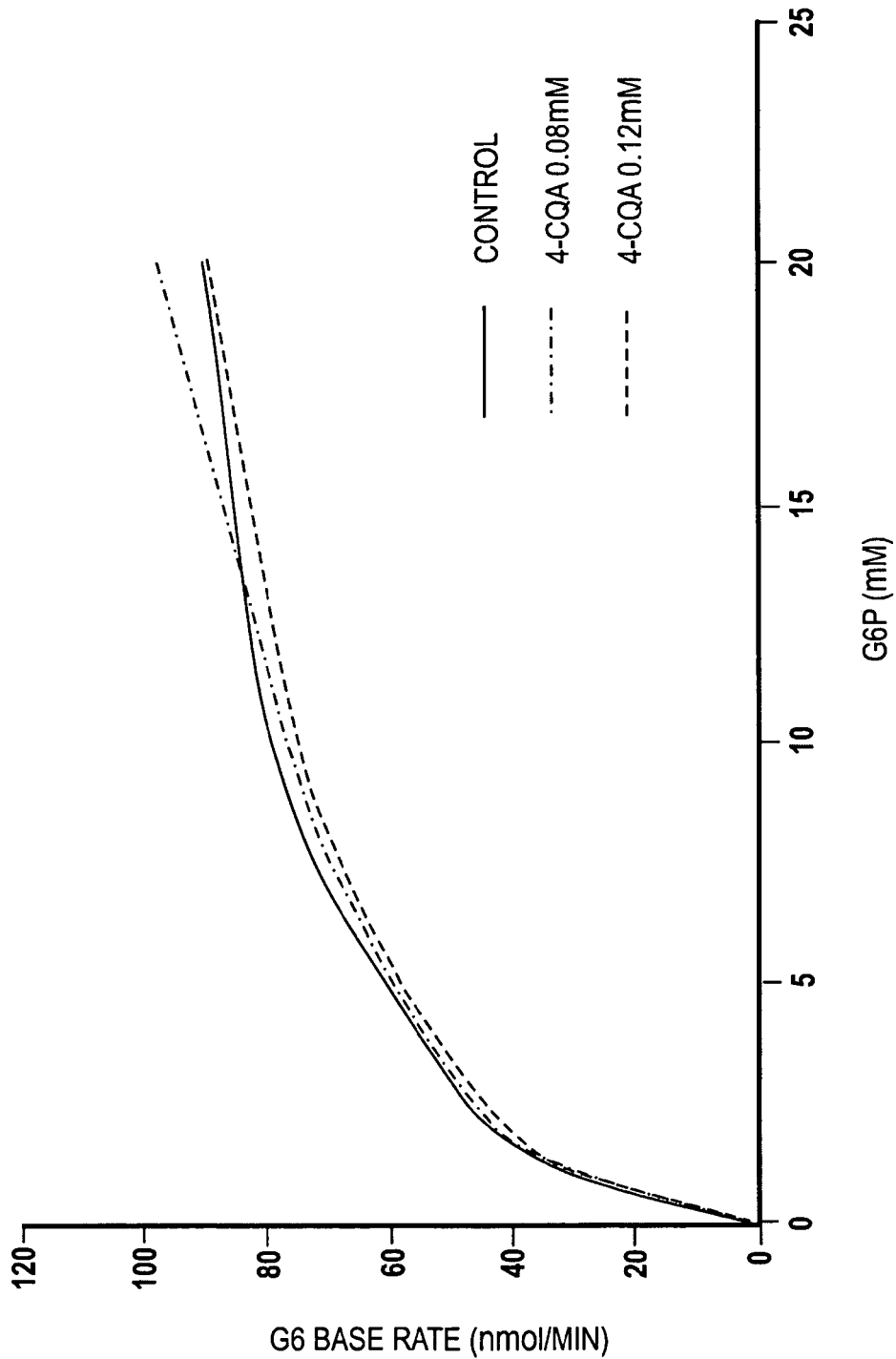
FIG. 13 illustrates the activity of glucose-6-phosphatase in intact human microsomes with or without 4-caffeoylquinic acids tested alone. Values are mean+/−SD. *p<0.05; p<0.01; *p<0.001 vs control.
Figure 14:
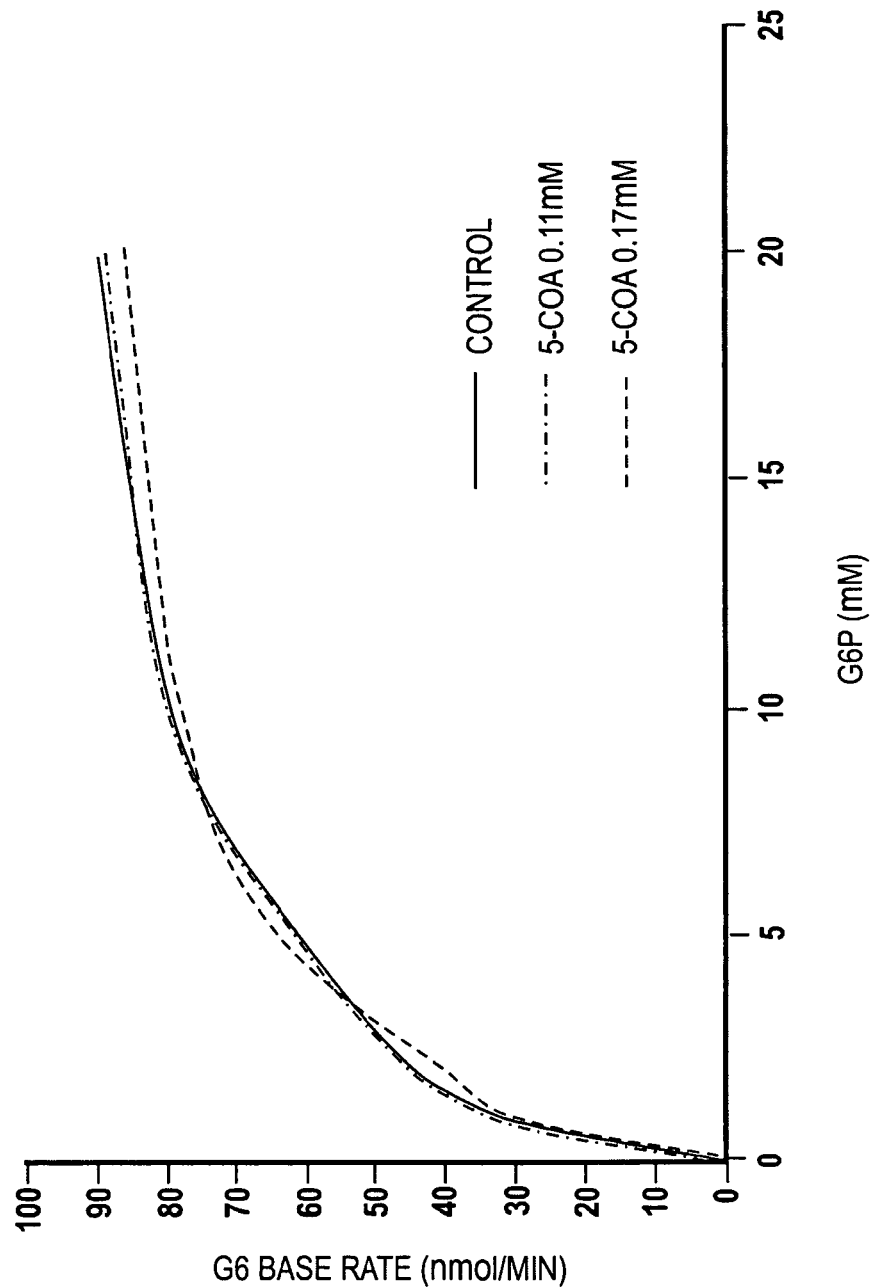
FIG. 14 illustrates the activity of glucose-6-phosphatase in intact human microsomes with or without 5-caffeoylquinic acid (5-CQA) tested alone. Values are mean+/−SD. *p<0.05; p<0.01; *p<0.001 vs control.
Figure 15:
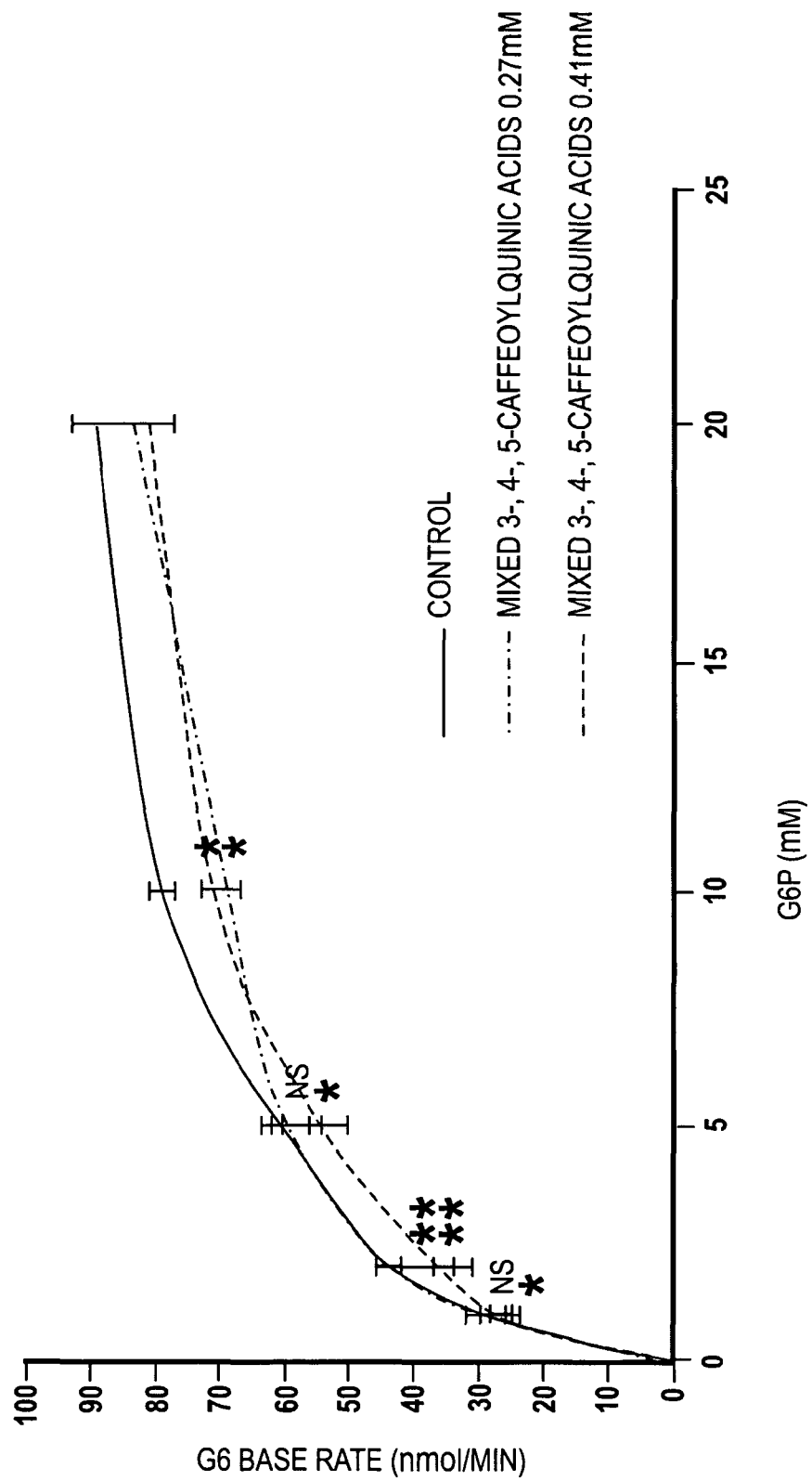
FIG. 15 illustrates the activity of glucose-6-phosphatase in intact human microsomes with or without 3-; 4-; 5-caffeoylquinic mixed together. Values are mean+/−SD. *p<0.05; p<0.01; *p<0.001 vs control.

Intact microsomes permit detection of the effect of the green coffee extract (Svetol® green coffee extract, NATUREX) and chlorogenic acids towards a Glc-6-Pase translocase, denoted T1, which facilitates penetration of glucose-6-phosphate into the endoplasmic reticulum. Such as for disrupted microsomes and whatever the concentration of the green coffee extract (Svetol® green coffee extract, NATUREX) tested, it inhibits significantly the translocase but not in a dose-dependent manner ($p<0.001$ vs control; FIG. 11). Surprisingly, when purified chlorogenic acids were tested separately, none of them had an activity towards the transporter T1 (FIGS. 12, 13, 14 and 15). When chlorogenic acids are mixed, the inhibition is significant compared to the control ($p<0.05$ or $p<0.01$ vs control). Such as for disrupted microsomes the sum of these activities explained a part of the green coffee extract (Svetol® green coffee extract, NATUREX) effect but not the totality suggesting that the caffeoyferuloylquinic acids present in the green coffee extract (Svetol® green coffee extract, NATUREX) are probably also active towards the translocase.

At the conclusion of this study, it appeared that the green coffee extract (Svetol® green coffee extract, NATUREX) is able to inhibit the catalytic site and the translocase of the Glc-6-Pase. 3-, 4- and 5-caffeoylquinic acids present in the green coffee extract (Svetol® green coffee extract, NATUREX) explains a part of the extract's activity but not the totality, suggesting that the caffeoyferuloylquinic acids present in the green coffee extract also probably have an activity towards this enzymatic system.

Until now, only 5-caffeoylquinic acid (5-CQA) was tested. The present invention shows for the first time that 3- and 4-caffeoylquinic acids are more active than 5-caffeoylquinic acid. Moreover, the major part of the green coffee extract (Svetol® green coffee extract, NATUREX) activity being explained by the sum of the pure molecule activity, the standardization of the extract in these molecules but also in total chlorogenic acids (including caffeoyferuloylquinic acids) is very important to develop an extract with health reproducible effect.

Example 5

Bioavailability of Total Chlorogenic Acids of a Green Coffee Extract (Svetol® Green Coffee Extract, NATUREX) in Humans The objective of this study was to evaluate the pharmacokinetic profiles of CGA compounds and metabolites in human plasma and urine after the acute consumption of a decaffeinated green coffee extract and to estimate the apparent bioavailability of CGA in this food matrix.

A preliminary test on 2 volunteers administrated with 400 mg and 1,000 mg of a green coffee extract (Svetol® green coffee extract, NATUREX) showed that doses up to 400 mg did not increase the concentration of total caffeoylquinic acids (tCQA), total caffeoyferuloylquinic acids (tdiCQA), and total chlorogenic acids (tCGA) in plasma (Table 7). These result evidence saturation at concentrations up to 400 mg in humans. Therefore, 400 mg can be considered a suitable dose of green coffee extract (Svetol® green coffee extract, NATUREX) in order to guarantee an appropriate tCGA concentration in human plasma.

TABLE 7

Pharmacokinetic parameters of chlorogenic acids compounds identified in plasma during 2 h after consumption of 400 mg and 1,000 mg of a green coffee extract (Svetol ® green coffee extract, NATUREX).

| Dose | tCQA | tdiCQA | tCGA |
|---|---|---|---|
| Volunteer 1 | | | |
| 400 mg | 6.06 | 5.67 | 11.73 |
| 1,000 mg | 5.99 | 2.65 | 8.64 |
| Volunteer 2 | | | |
| 400 mg | 7.41 | 2.50 | 9.91 |
| 1,000 mg | 4.26 | 1.93 | 6.19 |

In a further phase of the study, ten non-smoker volunteers (22-55 y), five male and five female, were recruited. Subjects were instructed to avoid consumption of phenolic-containing foods during the 48 h prior to the study. They were asked to eat only animal foods, refined cereal foods and artificial beverages. On the day of the study, after 10-12 h overnight fasting, an I.V. catheter was inserted into the antecubital vein and a baseline heparinized blood sample was obtained. 400 mg green coffee extract (Svetol® green coffee extract, NATUREX) were offered to each subject and sequential blood draws were obtained 0.5; 1; 2; 3; 4; 5; 6; 7 and 8 h after the capsules consumption. Blood samples were collected into heparin-containing tubes. Baseline blood aliquots were used to determine hematocrit and hemoglobin levels by standard methods. Plasma samples were obtained by centrifugation of the blood samples immediately after being drawn. Urine samples were also collected at baseline interval (minus 2-0 h) and at intervals of 0-2 h; 2-4 h; 4-6 h and 6-8 h after coffee consumption into appropriate plastic containers. Total urine volume was measured for each collection period. Plasma and urine aliquots for determination of CGA were acidified with HCl and kept frozen in liquid nitrogen until analyses. Urine aliquots for determination of creatinine were acidified with HCl and kept at −20.degree. C. until analyses. Every hour, starting one hour after green coffee extract consumption, subjects ate a CGA-free snack composed of white bread (25 g) with cream cheese (15 g) and 100 mL of a saline solution containing 0.21 g of NaCl, 2.28 g of glucose, 0.22 g of potassium citrate monohydrate and 0.1 g of sodium citrate di-hydrate, until the end of blood draws.

Analyses of CGA (including CGA lactones and caffeoyltryptophan) in the green coffee extract (Svetol® green coffee extract, NATUREX), plasma and urine were performed by HPLC and LC-DAD-MS gradient systems as described in detail by Farah et al. (J Agric Food Chem. 2006; 54:374-81) and Monteiro et al (J Nutr.; 137:2196-201). The detection limit for 5-CQA (4-fold baseline noise) under the conditions used in this study was 0.01 µg/mL. Results of CGA and phenolic acids in urine were normalized by creatinine excretion. Molar ratios of specific CGA compounds were calculated in green coffee extract as ratios of total amounts and, in plasma, as ratios of the corresponding AUC.

After green coffee extract (Svetol® green coffee extract, NATUREX) consumption, 3-CQA, 4-CQA, 5-CQA, 3,4-diCQA, 3,5-diCQA and 4,5-diCQA were identified in the plasma of all subjects. Such compounds represented together about 82% of CGA composition of the green coffee extract. Caffeic, ferulic, isoferulic and p-coumaric acids, which were not detected in the encapsulated extract, were present in the plasma of different subjects after green coffee extract consumption, contributing to 6.6%, 6.2%, 6.1% and 1.4% of total phenolics in plasma respectively.

$C_{max}$, $T_{max}$ and AUC of the CGA and cinnamic acids identified in plasma of the 10 subjects after green coffee extract consumption are shown in Table 8. CGA $C_{max}$ and $T_{max}$ varied largely among the subjects; $C_{max}$ of total CQA varied from 0.6 to 16.9 µmol/L, $C_{max}$ of total diCQA varied from 0.3 to 22.8 µmol/L, whereas $C_{max}$ of total CGA varied from 1.2 to 39.7 µmol/L, with mean concentrations of 8.2, 6.6 and 14.8 µmol/L, respectively. $T_{max}$ for total CQA, total diCQA and total CGA varied considerably among the subjects (from 0.5 to 8 h), with mean values of 3.3; 3.2 and 3.1 h, respectively.

Regarding individual compounds, 5-CQA was the major CGA identified in the plasma of all subjects at all time points after green coffee extract consumption, as indicated by both $C_{max}$ and AUC of 5-CQA. Considering mean values of plasma AUC, 5-CQA, 4-CQA and 3-CQA contributed with 31.3%, 7.5% and 5.2% of AUC of total phenolic compounds in plasma.

Molar ratios among CGA compounds were calculated considering their content in the green coffee extract and the AUC in plasma. For CQA, ratios of 5-CQA:4-CQA:3-CQA in the green coffee extract were 1.2:1.0:1.1, whereas their corresponding ratios in plasma were 6.0:1.4:1.0. The molar ratios 3,5-diCQA:4,5-diCQA:3,4-diCQA in the coffee extract were 1.0:1.6:1.7, while in plasma the ratios were 1.7:1.4:1.0, respectively. Moreover, comparing both CGA classes, the molar ratio diCQA:CQA in plasma was 6.2.times. higher than in the green coffee extract.

TABLE 8

Pharmacokinetic parameters of chlorogenic acids
and hydroxycinnamic acids identified in plasma
after decaffeinated green coffee consumption.

| Compound | Cmax (μmol/L) | Tmax (h) | AUC (μmol · h/L) |
|---|---|---|---|
| 3-caffeoylquinic acid | 0.9 ± 1.4 | 4.0 ± 2.6 | 3.0 ± 4.5 |
| 4-caffeoylquinic acid | 1.4 ± 1.1 | 3.6 ± 2.2 | 4.3 ± 5.4 |
| 5-caffeoylquinic acid | 5.9 ± 4.2 | 3.3 ± 2.4 | 17.9 ± 15.3 |
| 3,4-caffeoylferuloylquinic acid | 1.5 ± 1.6 | 2.6 ± 1.8 | 5.0 ± 4.9 |
| 3,5-caffeoylferuloylquinic acid | 2.7 ± 2.7 | 3.2 ± 2.5 | 8.7 ± 8.3 |
| 4,5-caffeoylferuloylquinic acid | 2.5 ± 3.0 | 3.3 ± 2.5 | 6.8 ± 5.7 |
| Total caffeoylquinic acids | 8.2 ± 6.3 | 3.3 ± 2.4 | 25.2 ± 24.4 |
| Total caffeoyferuloylquinic acids | 6.6 ± 6.9 | 3.2 ± 2.5 | 20.4 ± 17.5 |
| Total chlorogenic acids | 14.8 ± 11.7 | 3.1 ± 2.6 | 45.6 ± 37.1 |
| Caffeic acid | 1.1 ± 0.9 | 3.6 ± 2.1 | 3.8 ± 3.2 |
| Ferulic acid | 0.8 ± 0.3 | 2.9 ± 1.8 | 3.6 ± 1.5 |
| Isoferulic acid | 0.9 ± 0.2 | 2.9 ± 1.8 | 3.5 ± 1.9 |
| p-coumaric acid | 0.4 ± 0.03 | 2.5 ± 1.8 | 0.8 ± 0.2 |

Values are Mean ± SD, n = 10. $C_{max}$—Maximum plasma concentration; $T_{max}$—Time corresponding to $C_{max}$; AUC—Area under the curve.

Most subjects presented phenolic compounds in their baseline urine. Trace amounts of 5-CQA were observed in 5 subjects, with contents varying up to 0.35 μmol. Sinapic, gallic, p-hydroxybenzoic, and dihydrocaffeic acids were the major phenolic compounds at baseline, representing about 82% of the total amount of the identified phenolic compounds, which varied from 2.6 to 97.0 μmol among the subjects. The urinary excretion of phenolic compounds increased in 9 of 10 subjects after green coffee extract consumption. The total urinary excretion (μmol) of phenolic compounds for each subject before and after green coffee consumption, corrected by creatinine values is shown in Table 9. As with plasma, a large inter-individual variation was observed in the urinary excretion of all compounds after green coffee extract consumption. The only intact CGA compounds identified in urine after the extract consumption were 5-CQA and 4-CQA (0.41 to 4.02 μmol of 5-CQA and 0.83 to 1.22 μmol of 4-CQA). Not only at baseline but also after the extract consumption, sinapic, gallic, p-hydroxybenzoic, and dihydrocaffeic acids were the major phenolic compounds, representing, on average, 85% of the total amount of phenolic compounds identified in urine. Protocatechuic, dihydroferulic, benzoic and hippuric acids, which have been previously identified in urine after CGA consumption, were not identified in the urine of any of the subjects before or after the extract consumption.

In conclusion, these results increase evidence that at least CQA and diCQA, which are major CGA compounds from coffee absorbed in the human body, are being differentially absorbed and/or metabolized throughout the whole gastrointestinal tract. These results also confirm that urine is not a major excretion pathway of intact CGA compounds and their metabolites, and identifies sinapic, gallic, p-hydroxybenzoic, and dihydrocaffeic acids as major urinary metabolites of CGA in humans. In addition, this study shows that the major CGA compounds present in green coffee matrix are highly bioavailable in humans. A large inter-individual variation clearly exists in CGA absorption and/or metabolism in humans and requires further investigation regarding differences in genetic polymorphisms.

TABLE 9

Total Urinary excretion of CGA and metabolites in each subject after decaffeinated green coffee consumption.

| | Gallic Acid | ρ-Hydroxy-benzoic acid | Dihydro-caffeic acid | Vanillic acid | Siringic acid | Sinapic acid | 5-CQA | 4-CQA | Caffeic acid | Ferulic acid | Iso-ferulic acid | ρ-coumaric acid | Total Phenolics |
|---|---|---|---|---|---|---|---|---|---|---|---|---|---|
| 1-Baseline | 9.24 | 4.94 | 2.98 | 2.61 | 0.04 | 1.26 | Nd | Nd | Nd | 0.45 | 0.01 | 0.01 | 21.54 |
| 0-8 h | 43.47 | 32.58 | 29.97 | 10.38 | 3.85 | 10.50 | Nd | Nd | 0.11 | 2.24 | 0.92 | 0.13 | 134.15 |
| 2-Baseline | 3.55 | 1.08 | 0.25 | 1.86 | 0.47 | 0.97 | Nd | Nd | Nd | 0.13 | 0.02 | 0.01 | 8.34 |
| 0-8 h | 18.67 | 24.14 | 15.81 | 16.37 | 11.07 | 17.52 | 0.42 | Nd | 0.86 | 3.33 | 1.02 | 0.14 | 109.35 |
| 3-Baseline | 1.86 | 2.56 | Nd | 3.31 | 3.52 | 2.22 | 0.02 | Nd | 0.01 | 0.23 | 0.07 | 0.03 | 13.81 |
| 0-8 h | 9.41 | 27.94 | 56.05 | 24.27 | 16.51 | 13.34 | 0.41 | Nd | 0.07 | 4.96 | 2.16 | 0.07 | 155.18 |
| 4-Baseline | 0.70 | 0.28 | 0.16 | 0.41 | 1.62 | 1.43 | Nd | Nd | 0.03 | 0.55 | 0.02 | Nd | 5.22 |
| 0-8 h | 7.98 | 4.69 | 13.60 | 9.47 | 16.63 | 12.08 | 0.60 | Nd | 0.21 | 4.60 | 1.98 | 0.03 | 71.86 |
| 5-Baseline | 10.19 | 1.78 | 5.02 | 9.42 | 13.11 | 20.28 | Nd | Nd | Nd | 1.94 | 0.14 | Nd | 61.89 |
| 0-8 h | 25.45 | 16.65 | 15.09 | 21.20 | 9.35 | 47.67 | 0.46 | Nd | 0.40 | 6.43 | 1.87 | Nd | 144.56 |
| 6-Baseline | 10.57 | 12.03 | 4.25 | 2.73 | 0.34 | 19.55 | 0.04 | 0.04 | 0.09 | Nd | Nd | Nd | 49.63 |
| 0-8 h | 115.87 | 189.74 | 61.33 | 12.94 | 1.52 | 130.47 | 2.33 | 0.90 | 1.41 | 1.76 | 4.68 | 2.84 | 527.23 |
| 7-Baseline | 0.25 | 4.12 | 2.13 | 0.19 | 1.36 | 0.98 | Nd | Nd | Nd | Nd | Nd | Nd | 9.03 |
| 0-8 h | 14.03 | 26.72 | 19.10 | 5.63 | 15.08 | 19.94 | 4.02 | 0.91 | 3.28 | 1.17 | 2.15 | 0.92 | 116.06 |
| 8-Baseline | 6.79 | 12.12 | 27.54 | Nd | 3.64 | 0.87 | 0.35 | Nd | 0.40 | 0.09 | 0.73 | 0.03 | 52.57 |
| 0-8 h | 68.21 | 50.45 | 67.45 | 0.58 | 25.62 | 15.06 | 1.22 | 0.83 | 3.60 | 2.39 | 11.80 | 0.10 | 249.35 |
| 9-Baseline | 1.68 | 1.49 | 3.00 | 3.08 | 1.58 | 5.32 | 0.01 | Nd | 0.11 | 0.03 | 0.51 | Nd | 14.31 |
| 0-8 h | 57.69 | 48.45 | 97.73 | 2.26 | 7.94 | 161.54 | 1.67 | 0.86 | 5.35 | 5.80 | 17.00 | 1.81 | 408.92 |
| 10-Baseline | 25.25 | 19.91 | 12.71 | 0.86 | Nd | 39.11 | 0.21 | Nd | 1.72 | 0.21 | 4.83 | 0.05 | 104.86 |
| 0-8 h | 112.22 | 146.38 | 73.92 | 3.20 | Nd | 178.79 | 1.75 | 1.22 | 9.43 | 3.83 | 18.78 | 9.76 | 559.29 |

Results (μmol) are expressed as total excretion before and during 8 h after decaffeinated green coffee consumption; Nd = not detected.

Example 6

Hypoglycemic Effect of Coffee Extracts in Humans

The aim of this study was to evaluate the acute hypoglycemic effect of coffee extracts (*Thom. J Int Med Res* 2007; 35:900-908). The study was designed as a three way double-blind randomized crossover study with each subject serving as his or her own control. The products tested are shown in Table 10. 12 volunteers were recruited (BMI<25 kg/m$^2$). After overnight fasting an oral glucose tolerance test (placebo) was performed on all volunteers. Glucose levels were followed for 2 h after intake with measurements at 15, 30, 45, 60, 90 and 120 min and they were immediately randomized to one of the treatments, with glucose levels again followed for 2 h after intake with measurements at 15, 30, 45, 60, 90 and 120. There was a 1 week washout period between the different treatments.

TABLE 10

Coffee products tested

| Sample | Species | Ingredients | Dose |
| --- | --- | --- | --- |
| Control | | | 25 g sucrose + 400 ml water |
| Product A | C. arabica + C. robusta | 91% | 10 g Product A + 25 g sucrose + 400 ml water |
| | C. robusta (Svetol ® green coffee extract, NATUREX) | 9% | |
| Product B | | | 10 g Product B + 25 g sucrose + 400 ml water |
| Product C | | | 10 g Product C + 25 g sucrose + 400 ml water |

The results for the glycemic-AUC are shown in Table 11. 10 g of the Product A, Coffee Slender®, containing 900 mg of Svetol® green coffee extract (NATUREX) significantly reduced in 6.9% the glycemic-AUC compared to the placebo group (P<0.05).

TABLE 11

Mean ± SE area under the curve (AUC) data for plasma glucose concentration over 120 min study period following intake of samples and a glucose challenge.

| | Control | Product A | Product B | Product C |
| --- | --- | --- | --- | --- |
| Plasma glucose AUC | 778 ± 10.2 | 724 ± 8.2* | 788 ± 10.1 | 818 ± 10.9 |

*P < 0.05

Example 7

Body Weight and Body Fat Loss Effects of Coffee Extracts in Humans

The aim of this study was to evaluate the body weight and body fat loss effects of coffee extracts (*Thom. J Int Med Res* 2007; 35:900-908). The study was designed as a double-blind randomized study. The products tested are shown in Table 12. 30 volunteers were recruited (BMI 27.5-32.0 kg/m$^2$). 15 received the Product A, and 15 received the Product B during 12 weeks.

TABLE 12

Coffee products tested

| Sample | Species | Ingredients | Dose |
| --- | --- | --- | --- |
| Product A | C. arabica + C. robusta | 91% | 11 g Product A, in five cups per day |
| | C. robusta (Svetol ® green coffee extract, NATUREX) | 9% | |
| Product B | | | 11 g Product B, in five cups per day |

The results for the body weight loss are shown in Table 13 and the results for the body fat are shown in Table 14. 11 g of the Product A, Coffee Slender®., containing 1,000 mg of Svetol® green coffee extract (NATUREX) significantly reduced in 5.4 kg the body weight and in 3.6% the body fat compared to the placebo group (P<0.05) after 12 weeks of administration.

TABLE 13

Mean ± SE weight for overweight volunteers taking 2 kind of coffee extracts.

| | Weight (kg) | | | | |
| --- | --- | --- | --- | --- | --- |
| | Start | Week 4 | Week 12 | Start – Week 12 | P-value |
| Product A | 82.2 ± 4.5 | 83.6 ± 4.1 | 79.8 ± 3.9 | 5.4 ± 0.6 | P < 0.05 |
| Product B | 84.3 ± 4.3 | 83.7 ± 4.1 | 81.6 ± 4.2 | 1.7 ± 0.9 | NS |

TABLE 14

Mean ± SE percentage of body fat for overweight volunteers taking 2 kind of coffee extracts.

| | Body fat (%) | | | | |
| --- | --- | --- | --- | --- | --- |
| | Start | Week 4 | Week 12 | Start – Week 12 | P-value |
| Product A | 27.2 ± 2.0 | 25.6 ± 1.8 | 23.6 ± 1.7 | 3.6 ± 0.3 | P < 0.05 |
| Product B | 26.9 ± 2.1 | 26.7 ± 2.0 | 26.2 ± 2.0 | 0.7 ± 0.4 | NS |

Example 8

Inhibition of Hepatic Glucose-6-Phosphatase System (Glc-6-Pase System) by a Decaffeinated Green Coffee Extract (Svetol® Green Coffee Extract, NATUREX)

The aim of Example 8 was to determine the inhibitory activity of Svetol®, a decaffeinated green coffee extract that has a specific ratio between 5-CQA and other CGAs, on Glc-6-Pase hydrolysis in intact human liver microsomes. A secondary purpose of Example 8 was to determine the inhibitory effects of a series of structurally-related compounds in Svetol®, such as caffeoylquinic acids and caffeoyferuloylquinic acids. Example 8 tested whether Svetol® could inhibit the hepatic Glc-6-Pase system by measuring enzymatic activity in human liver microsomes. These experiments were conducted with or without Svetol® at final CGA concentrations of 0.2, 0.4 and 0.6 mM. The effect of Svetol® on Glc-6-Pase activity was tested as a function of Glc-6-Pase substrate concentration (2-10 mM). Example 8 also demonstrates below the importance of the position of the caffeoyl residue in the inhibition of Glc-6-Pase system by CGAs.

Chemicals: Svetol® (ref. GA501071, batch 252/10/A9) was supplied by Naturex (Avignon, France). Ascorbic acid; cacodylic acid; D-glucose 6-phosphate sodium salt; 5-CQA; ammonium molybdate tetrahydrate; potassium phosphate; and sodium dodecyl sulfate were purchased from Sigma (Saint Quentin Fallavier, France). Pooled human liver microsomes were obtained from BD Biosciences (Le Pont le Claix, France) and stored at −80° C. until use. Standards for caffeoylquinic and caffeoyferuloylquinic acids were supplied by Chengdu Biopurify Phytochemicals LTD (Chengdu, China).

Svetol® is a commercial unroasted and decaffeinated green *Coffea canephora* extract, standardized to contain >45% CGAs and >10% 5-CQA. Table 15 lists the average contents and standard deviations of CGAs in five industrial batches that have been quantified as 5-CQA equivalents (batches 252/10/A9, H43/17/A8, H37/40/A9, 327/23/A9 and 324/44/A9; Naturex). The sample in Table 15 contains high levels of total CGAs (47.66% of dry weight) with a specific ratio (0.3) between 5-CQA and total CGAs.

TABLE 15

Chlorogenic Acid Content in Svetol ®

| Compound | Typical content in Svetol ® (%) | Sample (%) |
|---|---|---|
| 3-CQA | 6.53 ± 0.54 | 6.61 |
| 4-CQA | 7.31 ± 0.43 | 7.66 |
| 5-CQA | 14.72 ± 1.07 | 13.83 |
| 3,4-diCQA | 3.57 ± 0.54 | 3.34 |
| 3,5-diCQA | 2.38 ± 0.08 | 2.38 |
| 4,5-diCQA | 4.22 ± 0.15 | 4.15 |
| 3-FQA | 1.28 ± 0.11 | 1.30 |
| 4-FQA | 0.50 ± 0.23 | 1.87 |
| 5-FQA | 3.39 ± 0.36 | 3.39 |
| 3,4-caffeoylferuloylquinic acid | 0.67 ± 0.06 | 0.77 |
| 3,5-caffeoylferuloylquinic acid | 0.30 ± 0.02 | 0.31 |
| 4,5-caffeoylferuloylquinic acid | 0.30 ± 0.29 | 0.81 |
| caffeoyltryptophan | 1.00 ± 0.80 | 1.23 |

HPLC Analysis of CGAs in Svetol® Analysis of CGAs in Svetol® was performed using the HPLC-diode array detector gradient system (Agilent 1100 series). The chromatographic analysis was conducted with a Zorbax Eclipse XDBC18 4.6 50 mm column (1.8 μm). The solvents were H2O acetic acid (96:4, v/v) as solvent A and methanol/acetonitrile/acetic acid (60:10:2, v/v/v) as solvent B, at a flow rate of 1.2 mL/min with the following gradient: 5% B (0-1 min), 5-15% B (1-4 min), and 15-70% B (4-25 min).

Measurement of Glc-6-Pase Activity in Microsomes: Microsomal Glc-6-Pase activity was measured on the basis of the rate of release of phosphate under the assay conditions that were described by Wallert et al., Kinetic Analysis of Glucose-6-Phosphatase: An Investigative Approach to Carbohydrate Metabolism and Kinetics. *Biochem. Mol. Biol. Educ.* 2001, 29, 199-203. The enzyme assays were performed at 37° C. in a final volume of 320 .mu.L, containing 100 mM cacodylic acid, pH 6.5 and concentrations of the substrate Glc-6-Pase ranging from 2 to 10 mM.

The reaction was started by adding intact microsomes and was stopped with the addition of 3.2 mL of colorimetric reagent [9 volumes of molybdate (0.42% ammonium molybdate in 1 N $H_2SO_4$), 2 volumes of 5% SDS and 1 volume of 10% ascorbic acid, freshly prepared and stored on ice for a maximum of 6 h]. All samples were incubated for 30 minutes at 45° C., and the absorbance of the phosphate-molybdate complex was measured at 820 nm.

Microsomal intactness was quantified by measuring Man-6-Pase activity. Anion, W J. Measurement of intactness of rat liver endoplasmic reticulum. Methods Enzymol. 1989, 174, 58-67. In a preliminary study, Glc-6-Pase activity in intact human liver microsomes was determined on the basis of microsomal protein concentration and incubation time to obtain optimal experimental conditions, that is, 100 μg of microsomal proteins and 5 minutes of incubation (data not shown). Quantification was performed at optimal wavelengths (330 nm) for the CGAs during chromatographic separation. Samples were filtered (0.45 μm), and 2 μL was injected directly. The standard deviation for three analyses of the same sample was <5% for all compounds.

Preparation of Test Compounds: Stock solutions of test compounds were prepared in ultrapure water (pH 6.5) and diluted with assay reagent to the final concentrations.

Enzymatic activity was expressed as micromoles of phosphate released per minute per milligram of protein. Results were expressed as means±standard deviation (SD) of three independent experiments. Percentage of inhibition of Glc-6 Pase system activity was calculated by dividing the initial rate of reaction in microsomes that were treated with individual compounds by the initial rate of reaction in untreated microsomes. The contribution of individual CGAs to total inhibition by Svetol® was calculated on the basis of their concentrations in Svetol® and their own inhibition values by dividing the percentage of inhibition of each CGA by the percentage of inhibition of 0.6 mM total CGAs from Svetol® Statistical analysis was performed using an ANOVA test followed by a post hoc Tukey test under a normality assumption (Shapiro Wilk) or Kruskall Wallis nonparametric test followed by Bonferroni adjusted Mann-Whitney test otherwise; p<0.05 was considered to be significant.

Inhibition of Glc-6-Pase System Activity by Svetol®: The double-reciprocal plots in Table 16 show that Svetol® decreased Vm values in a dose-dependent manner, but Km was unchanged.

FIG. 16 illustrates a Double-reciprocal or Lineweaver-Burk plot of inhibition of Glc-6-Pase hydrolysis by Svetol® in human liver microsomes having a reaction mixture (pH 6.5) contained 2.0-10.0 mM Glc-6-Pase with 0 (■), 0.2 (♦), 0.4 (▲) or 0.6 mM (●) of Svetol®.

TABLE 17

Kinetic Parameters of Glc-6-Pase in Human Liver Microsomes.
Table 17: Kinetic Parameters of Glc-6-Pase in Human Liver Microsomes.

| Condition | $V_{max}$(μmol/min/mg protein) | $K_M$ (mM) |
|---|---|---|
| Control | 0.095 ± 0.002 | 2.41 ± 0.33 |
| Svetol ® (0.2 mM) | 0.082 ± 0.003* | 2.65 ± 0.18 |
| Svetol ® (0.4 mM) | 0.074 ± 0.007* | 2.96 ± 0.47 |
| Svetol ® (0.6 mM) | 0.068 ± 0.001* | 2.99 ± 0.25 |

Data are expressed as mean of triplicate (SD. *indicates values that are significantly different from control (P < 0.001).

By Michaelis-Menten kinetics, Svetol® inhibited Glc-6-Pase hydrolysis in human liver microsomes in a significant and competitive manner (Table 17), which is consistent with previous studies of 5-CQA in rat liver microsomes in Anion, W. J., et al., *Chlorogenic acid and hydroxynitrobenzaldehyde: new inhibitors of hepatic glucose 6-phosphatase*. Arch. Biochem. Biophys. 1997, 339, 315-322.

Other studies have demonstrated that 5-CQA and its synthetic analogues inhibit Glc-6-Pase, such as Anion et al., *Chlorogenic acid and hydroxynitrobenzaldehyde: new* inhibitors of hepatic glucose 6-*phosphatase*. Arch. Biochem. Biophys. 1997, 339, 315-322; Hemmerle et al., *Chlorogenic acid and synthetic chlorogenic acid derivatives: novel inhibitors of hepatic glucose-6-phosphate translocase*. J. Med. Chem. 1997, 40, 137-145 and Anion et al. *Chlorogenic acid analog 53483: a potent competitive inhibitor of the hepatic andrenal glucose-6-phosphatase systems*. Arch. Biochem. Biophys. 1998, 351, 279-285. Thus, Example 8 investigated whether other CGAs in coffee possess the same functions as 5-CQA. Therefore, the selected CQAs and di-CQAs were studied at their respective concentrations in Svetol® (0.6 mM total CGAs) with 2 mM Glc-6-Pase (i.e., below the apparent K m) to facilitate detection of putative competitive inhibitors.

The percentages of inhibition of Glc-6-Pase hydrolysis of each compound and its contribution to the inhibitory activity of Svetol® are shown in Table 18. Of the three CQAs in Svetol®, 4-CQA, inhibited Glc-6-Pase hydrolysis to the greatest extent (14% inhibition). In addition, 4-CQA contributed 40% of the inhibitory effect of Svetol®. 4,5-diCQA effected similar inhibition as 4-CQA (13% inhibition) and contributed 35% of the inhibitory effect of Svetol®. The inhibition by mixtures of CQAs and diCQAs (at their respective proportions in Svetol®.) were also examined. When all CQAs and diCQAs were tested separately, similar inhibition was observed (approximately 20%). Moreover, when combined, the inhibition of Glc-6-P hydrolysis by 0.6 mM total CGAs from Svetol®. (36%) was recovered (35%), suggesting that no other compounds participate in Svetol-mediated inhibition.

TABLE 18

Structure, Percentage of Inhibition and Contribution of Chlorogenic Acids to Glc-6-Pase system Inhibition by Svetol ®. Each compound was tested at its naturally occurring concentration in 0.6 mM Svetol ®.

| Compound | Structure | Concentration tested (μM) | Percentage inhibition of G6Pase | Contribution (%) |
|---|---|---|---|---|
| 3-CQA | 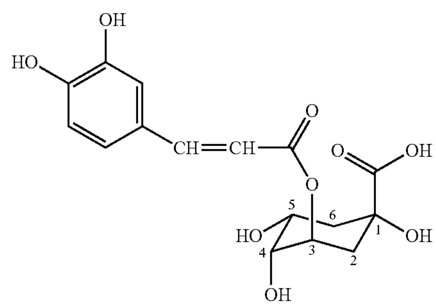 | 110 | 0 | 0 |
| 5-CQA | 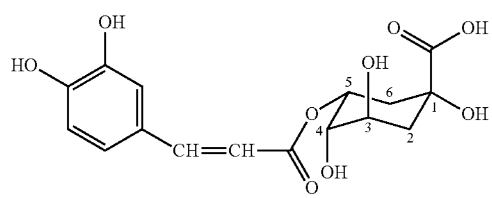 | 160 | 9.2 ± 1.4 | 25 |
| 4-CQA | 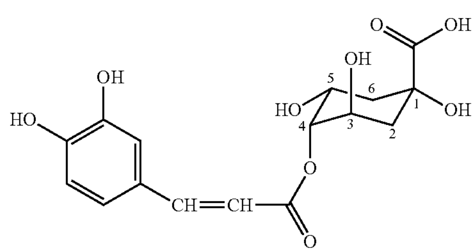 | 120 | 14.4 ± 1.2 | 40 |

TABLE 18-continued

Structure, Percentage of Inhibition and Contribution of Chlorogenic Acids to Glc-6-Pase system Inhibition by Svetol ®. Each compound was tested at its naturally occurring concentration in 0.6 mM Svetol ®.

| Compound | Structure | Concentration tested (µM) | Percentage inhibition of G6Pase | Contribution (%) |
| --- | --- | --- | --- | --- |
| 3,4-diCQA | [structure] | 33 | 6.9 ± 4.3 | 19 |
| 3,5-diCQA | [structure] | 20 | 0 | 0 |
| 4,5-diCQA | [structure] | 38 | 12.8 ± 2.6 | 35 |
| All CQA | | | 18.1 ± 5.5 | 50 |
| All di-CQA | | | 22.7 ± 1.5 | 62 |
| All CQA + all di-CQA | | | 34.8 ± 4.0 | 96 |

Starvation and diabetes cause a 2-3-fold increase in Glc-6-Pase activity in the liver, making this enzyme system a potential target for nutritional compounds that are intended, for example, to suppress hepatic glucose production to ameliorate diabetic hyperglycemia. Example 8 details the inhibition of Glc-6-Pase hydrolysis in intact human liver microsomes by Svetol®. Svetol® is a decaffeinated green coffee extract that has a high CGA content and a specific ratio between CQAs and diCQAs. Example 8 showed that CQAs and diCQAs, at their respective concentrations in Svetol®, have inhibitory effects similar to those of Svetol®, suggesting that they are the compounds that are solely responsible for Svetol® activity.

The structure-activity analysis in Example 8 showed that variation in the position of the caffeoyl residue is important for the inhibition of Glc-6-Pase hydrolysis. Notably, two compounds (3-CQA and 3,5-diCQA) were apparently ineffective in suppressing Glc-6-Pase hydrolysis, and greater inhibition was achieved with 4-CQA and 4,5-diCQA. This result suggests that the caffeoyl residue at position 3 has an unfavorable effect, whereas at position 4, it appears to be beneficial.

The observed 36% inhibition by Svetol® should contribute to its antidiabetic, glucose-lowering effects by reducing hepatic glucose production. On the basis of these and other published results (Anion et al.; Hemmerle et al.; and Anion, W. J.), the inventors propose a mechanism by which Svetol® acts. In combination with diet, it inhibits glucose absorption from the small intestine. Welsch et al., *Dietary phenolic compounds: inhibition of Na p-dependent D-glucose uptake in rat intestinal brush border membrane vesicles*. J. Nutr. 1989, 19, 1698-1704. Furthermore, by inhibiting Glc-6-Pase system activity, Svetol® could limit the release of glucose from glycogen into general circulation and prevent insulinemia, as reported in vivo with the chlorogenic acid derivative 53483 Herling et al., *Pharmacodynamic profile of a novel inhibitor of the hepatic glucose-6-phosphatase system*. Am. J. Physiol. 1998, 274, 1087-1093 and Simon et al., *Upregulation of hepatic glucose 6-phosphatase gene expression in rats treated with an inhibitor of glucose-6-phosphate translocase*. Arch. Biochem. Biophys. 2000, 373, 418-428. This mechanism, however, depends on the bioavailability of chlorogenic acid and its isomers. In rats, Lafay et al. showed that 5-CQA is not hydrolyzed in the stomach or small intestine but is absorbed in the stomach in its intact form and as caffeic and (iso) ferulic acids in the small intestine. Lafay et al. *Chlorogenic acid is absorbed in its intact form in the stomach of rats*. J. Nutr. 2006, 136, 1192-1197. Recently, Farah et al. confirmed that CQA and diCQA are differentially absorbed and metabolized throughout the entire gastrointestinal tract. Farah et al., *Chlorogenic acids from green coffee extract are highly bioavailable in humans*. J. Nutr. 2008, 138, 2309-2315. In addition, Farah et al. also provides evidence that urination is not a major excretion pathway of intact CGA compounds and their metabolites. In summary, Example 8 demonstrates the importance of the position of the caffeoyl residue in the inhibition of the Glc-6-Pase system by CGAs.

One skilled in the art will appreciate that the present invention can be practical by other than the embodiments described herein, which are presented for purposes of illustration and not of limitation.

We claim:

1. A method of inhibiting human liver glucose-6-phosphatase system (Glc-6-Pase) activity, the method comprising administering to an overweight human subject, or to a human subject having obesity or type 2 diabetes an effective amount of a composition consisting of 4-caffeoylquinic acid (4-CQA), 5-caffeoylquinic acid (5-CQA), 3,4-dicaffeoylquinic acid (3,4-diCQA), and 4,5-dicaffeoylquinic acid (4,5-diCQA) to inhibit the human liver Glc-6-Pase activity.

* * * * *